(12) United States Patent
Pfouts et al.

(10) Patent No.: US 8,377,001 B2
(45) Date of Patent: Feb. 19, 2013

(54) FEEDING SET FOR A PERISTALTIC PUMP SYSTEM

(75) Inventors: Mark D. Pfouts, Galena, OH (US); Martin Toolan, Sligo (IE)

(73) Assignee: Abbott Laboratories, Abbott Park, IL (US)

( * ) Notice: Subject to any disclaimer, the term of this patent is extended or adjusted under 35 U.S.C. 154(b) by 255 days.

(21) Appl. No.: 12/896,422

(22) Filed: Oct. 1, 2010

(65) Prior Publication Data

US 2012/0083736 A1   Apr. 5, 2012

(51) Int. Cl.
*A61M 5/168* (2006.01)

(52) U.S. Cl. ...... 604/151; 604/250; 604/256; 417/477.2

(58) Field of Classification Search ............. 604/67, 604/151–152, 250, 256; 417/43, 474, 476, 417/477.1, 477.2

See application file for complete search history.

(56) References Cited

U.S. PATENT DOCUMENTS

| | | |
|---|---|---|
| 5,259,367 A | 11/1993 | Kirby et al. |
| 5,263,475 A | 11/1993 | Altermatt et al. |
| 5,281,111 A | 1/1994 | Plambeck et al. |
| 5,290,520 A | 3/1994 | Maystre et al. |
| 5,322,073 A | 6/1994 | Michels et al. |
| 5,328,481 A | 7/1994 | Wang |
| 5,364,342 A | 11/1994 | Beuchat et al. |
| 5,413,565 A | 5/1995 | Michels et al. |
| 5,458,470 A | 10/1995 | Mannhart et al. |
| 5,470,210 A | 11/1995 | Larsen |
| 5,499,969 A | 3/1996 | Beuchat et al. |
| 5,542,921 A | 8/1996 | Meyers et al. |
| 5,553,485 A | 9/1996 | Kaabi et al. |
| 5,554,140 A | 9/1996 | Michels et al. |
| 5,588,815 A | 12/1996 | Zaleski, II |
| 5,595,175 A | 1/1997 | Malcher et al. |
| 5,611,464 A | 3/1997 | Tsao et al. |
| 5,628,753 A | 5/1997 | Cracauer et al. |
| 5,634,907 A | 6/1997 | Rani et al. |
| 5,662,928 A | 9/1997 | Braun |

(Continued)

FOREIGN PATENT DOCUMENTS

| | | |
|---|---|---|
| EP | 0120284 A1 | 10/1984 |
| EP | 0485342 A1 | 5/1992 |

(Continued)

OTHER PUBLICATIONS

International Search Report and Written Opinion of International Application No. PCT/US2011/052548; Dec. 12, 2011; 11 pages.

*Primary Examiner* — Quynh-Nhu H Vu

(57) ABSTRACT

A feeding set for a peristaltic pump system includes a cassette configured for releasable connection thereto. A deflectable lumen priming actuator is formed integrally with the cassette for conjoint connection to and disconnection from the pump system with the cassette as a single unit. The priming actuator includes an actuation pad and is moveable from a rest position to a deflected position. A substantially flexible lumen is coupled to the cassette. The lumen has an inlet, an outlet, and an extensible peristalsis loop. An inline valve is received within the lumen. The inline valve is arranged to obstruct fluid flow through the lumen. The actuation pad of the priming actuator is located proximate the inline valve in the rest position and is adapted to contact and apply a force to the lumen adjacent the inline valve when the priming actuator is moved to the deflected position. The force applied to the lumen is sufficient to establish at least one flow channel between the inline valve and the lumen.

25 Claims, 18 Drawing Sheets

U.S. PATENT DOCUMENTS

| | | | |
|---|---|---|---|
| 5,674,194 A | 10/1997 | Jung et al. | |
| 5,676,530 A | 10/1997 | Nazarifar | |
| 5,704,584 A * | 1/1998 | Winterer et al. | 251/7 |
| 5,747,824 A | 5/1998 | Jung et al. | |
| 5,764,539 A | 6/1998 | Rani | |
| 5,800,396 A | 9/1998 | Fanney et al. | |
| 5,827,984 A | 10/1998 | Sinnreich et al. | |
| 5,841,028 A | 11/1998 | Bray et al. | |
| 5,871,467 A | 2/1999 | Reuning et al. | |
| 5,885,243 A | 3/1999 | Capetan et al. | |
| 5,899,674 A | 5/1999 | Jung et al. | |
| 5,902,285 A | 5/1999 | Kudsk et al. | |
| 5,947,976 A | 9/1999 | Van Noy et al. | |
| 5,951,510 A | 9/1999 | Barak | |
| 5,961,488 A | 10/1999 | Barak | |
| 5,989,212 A | 11/1999 | Sussman et al. | |
| 5,997,499 A | 12/1999 | Sussman et al. | |
| 6,004,284 A | 12/1999 | Sussman et al. | |
| 6,032,073 A | 2/2000 | Effenhauser | |
| 6,039,714 A | 3/2000 | Cracauer et al. | |
| 6,042,564 A | 3/2000 | Barak | |
| 6,059,544 A | 5/2000 | Jung et al. | |
| 6,068,853 A | 5/2000 | Giannos et al. | |
| 6,080,128 A | 6/2000 | Sussman et al. | |
| 6,106,249 A | 8/2000 | Barak | |
| 6,109,572 A | 8/2000 | Urban et al. | |
| 6,110,162 A | 8/2000 | Sussman et al. | |
| 6,179,805 B1 | 1/2001 | Sussman et al. | |
| 6,179,808 B1 | 1/2001 | Boukhny et al. | |
| 6,196,989 B1 | 3/2001 | Padget et al. | |
| 6,206,848 B1 | 3/2001 | Sussman et al. | |
| 6,241,700 B1 | 6/2001 | Leukanech | |
| 6,258,053 B1 | 7/2001 | Mackool | |
| 6,261,283 B1 | 7/2001 | Morgan et al. | |
| 6,287,274 B1 | 9/2001 | Sussman et al. | |
| 6,293,926 B1 | 9/2001 | Sorensen et al. | |
| 6,315,755 B1 | 11/2001 | Sussman | |
| 6,319,223 B1 | 11/2001 | Wortrich et al. | |
| 6,331,171 B1 | 12/2001 | Cohen | |
| 6,332,877 B1 | 12/2001 | Michels | |
| 6,336,912 B1 | 1/2002 | Bourguignon | |
| 6,398,759 B1 | 6/2002 | Sussman et al. | |
| 6,416,777 B1 | 7/2002 | Yaacobi | |
| 6,428,502 B1 | 8/2002 | Lang | |
| 6,471,676 B1 | 10/2002 | DeLegge et al. | |
| 6,478,766 B1 | 11/2002 | Chon | |
| 6,491,661 B1 | 12/2002 | Boukhny et al. | |
| 6,561,999 B1 | 5/2003 | Nazarifar et al. | |
| 6,572,349 B2 | 6/2003 | Sorensen et al. | |
| 6,575,929 B2 | 6/2003 | Sussman et al. | |
| 6,579,270 B2 | 6/2003 | Sussman et al. | |
| 6,589,201 B1 | 7/2003 | Sussman et al. | |
| 6,589,204 B1 | 7/2003 | Sussman et al. | |
| 6,602,193 B2 | 8/2003 | Chon | |
| 6,631,650 B1 | 10/2003 | Espinosa | |
| 6,632,214 B2 | 10/2003 | Morgan et al. | |
| 6,648,847 B2 | 11/2003 | Sussman et al. | |
| 6,669,950 B2 | 12/2003 | Yaacobi | |
| 6,676,628 B2 | 1/2004 | Sussman et al. | |
| 6,740,074 B2 | 5/2004 | Morgan et al. | |
| 6,743,245 B2 | 6/2004 | Lobdell | |
| 6,770,056 B2 | 8/2004 | Price et al. | |
| 6,824,525 B2 | 11/2004 | Nazarifar et al. | |
| 6,843,780 B2 | 1/2005 | Larrain et al. | |
| 6,860,868 B1 | 3/2005 | Sussman et al. | |
| 6,863,073 B2 | 3/2005 | D'Amico et al. | |
| 6,868,720 B2 | 3/2005 | Lobdell et al. | |
| 6,875,194 B2 | 4/2005 | MacKool | |
| 6,908,451 B2 | 6/2005 | Brody et al. | |
| 6,921,385 B2 | 7/2005 | Clements et al. | |
| 6,955,073 B2 | 10/2005 | Morgan et al. | |
| 6,962,488 B2 | 11/2005 | Davis et al. | |
| 7,014,629 B2 | 3/2006 | Mackool | |
| 7,060,050 B2 | 6/2006 | Kliem et al. | |
| 7,070,578 B2 | 7/2006 | Leukanech et al. | |
| 7,121,143 B2 | 10/2006 | Malmstrom et al. | |
| 7,150,727 B2 | 12/2006 | Cise et al. | |
| 7,160,268 B2 | 1/2007 | Darnell et al. | |
| 7,169,755 B2 | 1/2007 | Shah et al. | |
| 7,172,578 B2 | 2/2007 | Mackool | |
| 7,192,419 B2 | 3/2007 | Larrain et al. | |
| 7,201,738 B1 | 4/2007 | Bengmark | |
| 7,226,435 B2 | 6/2007 | Darnell | |
| 7,244,240 B2 | 7/2007 | Nazarifar et al. | |
| 7,350,669 B2 | 4/2008 | Rani | |
| 7,351,219 B2 | 4/2008 | MacKool | |
| 7,392,144 B2 | 6/2008 | Sorensen et al. | |
| 7,393,189 B2 | 7/2008 | Davis et al. | |
| 7,484,769 B2 | 2/2009 | Domash et al. | |
| 7,509,831 B2 | 3/2009 | Khashayar | |
| 7,516,741 B2 | 4/2009 | Glusker et al. | |
| 7,524,299 B2 | 4/2009 | Hopkins et al. | |
| 7,559,914 B2 | 7/2009 | Domash et al. | |
| 7,569,149 B2 | 8/2009 | Koch et al. | |
| 7,572,242 B2 | 8/2009 | Boukhny | |
| 7,594,901 B2 | 9/2009 | Hopkins et al. | |
| 7,604,615 B2 | 10/2009 | Gao et al. | |
| 7,625,388 B2 | 12/2009 | Boukhny et al. | |
| 7,644,603 B2 | 1/2010 | Gordon et al. | |
| 7,645,255 B2 | 1/2010 | Gordon et al. | |
| 7,651,010 B2 | 1/2010 | Orzech et al. | |
| RE41,159 E | 3/2010 | Bourguignon | |
| 7,677,467 B2 | 3/2010 | Fink et al. | |
| 7,695,447 B2 | 4/2010 | Khashayar et al. | |
| 7,704,244 B2 | 4/2010 | Boukhny et al. | |
| 7,713,202 B2 | 5/2010 | Boukhny et al. | |
| 7,713,228 B2 | 5/2010 | Robin | |
| 7,727,193 B2 | 6/2010 | Boukhny et al. | |
| 7,740,619 B2 | 6/2010 | Pinedjian et al. | |
| 7,748,377 B2 | 7/2010 | Smith et al. | |
| 7,758,538 B2 | 7/2010 | Boukhny et al. | |
| 7,762,978 B2 | 7/2010 | Mackool | |
| 7,775,780 B2 | 8/2010 | Hopkins et al. | |
| 7,780,633 B2 | 8/2010 | Domash | |
| 7,783,346 B2 | 8/2010 | Smith et al. | |
| 7,785,782 B2 | 8/2010 | Chien et al. | |
| 7,811,255 B2 | 10/2010 | Boukhny et al. | |
| 7,814,905 B2 | 10/2010 | Schuler et al. | |
| 7,857,794 B2 | 12/2010 | Dimalanta et al. | |
| 2001/0004444 A1* | 6/2001 | Haser et al. | 417/477.2 |
| 2005/0178206 A1* | 8/2005 | Malmstrom et al. | 73/705 |
| 2005/0209552 A1 | 9/2005 | Beck et al. | 604/67 |
| 2006/0058740 A1* | 3/2006 | Cise et al. | 604/247 |
| 2009/0053085 A1 | 2/2009 | Thompson et al. | |
| 2010/0082001 A1 | 4/2010 | Beck et al. | |
| 2010/0100060 A1 | 4/2010 | Turner | |
| 2010/0152700 A1 | 6/2010 | Paine | |
| 2010/0163021 A1 | 7/2010 | Lai | |
| 2010/0174241 A1 | 7/2010 | Ebbett et al. | |
| 2010/0282247 A1 | 11/2010 | Kadrichu et al. | |
| 2010/0298812 A1 | 11/2010 | Wolkenstorfer | |
| 2011/0004190 A1* | 1/2011 | Cise et al. | 604/500 |
| 2011/0022023 A1 | 1/2011 | Weitzel et al. | |
| 2012/0083737 A1* | 4/2012 | Beck | 604/151 |

FOREIGN PATENT DOCUMENTS

| | | |
|---|---|---|
| EP | 0488609 A1 | 6/1992 |
| EP | 0540465 A1 | 5/1993 |
| EP | 0736287 A1 | 10/1996 |
| EP | 0559602 B1 | 4/1997 |
| EP | 0627904 B1 | 11/1997 |
| EP | 0733375 B1 | 9/1998 |
| EP | 0657180 B1 | 11/1999 |
| EP | 0812176 B1 | 12/1999 |
| EP | 0962204 A1 | 12/1999 |
| EP | 0732114 B1 | 8/2000 |
| EP | 1027900 A1 | 8/2000 |
| EP | 0776670 B1 | 9/2001 |
| EP | 0774266 B1 | 10/2001 |
| EP | 0786260 B1 | 12/2001 |
| EP | 1166818 A1 | 1/2002 |
| EP | 1062958 B1 | 4/2002 |
| EP | 0861654 B1 | 5/2002 |
| EP | 1099854 B1 | 5/2002 |
| EP | 0774267 B1 | 6/2002 |
| EP | 0923394 B1 | 6/2002 |
| EP | 0929331 B1 | 9/2002 |

| | | | | | | |
|---|---|---|---|---|---|---|
| EP | 1285642 | A1 | 2/2003 | WO | 9735886 A1 | 10/1997 |
| EP | 0777111 | B1 | 9/2003 | WO | 9825557 A1 | 6/1998 |
| EP | 0962203 | B1 | 9/2003 | WO | 9837856 A1 | 9/1998 |
| EP | 1187643 | B1 | 9/2003 | WO | 9846293 A1 | 10/1998 |
| EP | 0872252 | B1 | 10/2003 | WO | 9846294 A1 | 10/1998 |
| EP | 1356833 | A1 | 10/2003 | WO | 9847551 A1 | 10/1998 |
| EP | 1080739 | B1 | 3/2004 | WO | 0035461 A1 | 6/2000 |
| EP | 0962205 | B1 | 7/2004 | WO | 0047250 A1 | 8/2000 |
| EP | 1466646 | A1 | 10/2004 | WO | 0078372 A1 | 12/2000 |
| EP | 1320393 | B1 | 11/2004 | WO | 0123277 A1 | 4/2001 |
| EP | 1221919 | B1 | 2/2005 | WO | 0128474 A1 | 4/2001 |
| EP | 1299149 | B1 | 9/2005 | WO | 0152921 A2 | 7/2001 |
| EP | 1251894 | B1 | 12/2005 | WO | 0200291 A1 | 1/2002 |
| EP | 1356835 | B1 | 1/2006 | WO | 03024519 A1 | 3/2003 |
| EP | 1526824 | B1 | 2/2006 | WO | 03068197 A1 | 8/2003 |
| EP | 1077736 | B2 | 3/2006 | WO | 2004012636 A2 | 2/2004 |
| EP | 1356834 | B1 | 6/2006 | WO | 2004012637 A1 | 2/2004 |
| EP | 1707166 | A1 | 10/2006 | WO | 2004035111 A2 | 4/2004 |
| EP | 1782781 | A1 | 5/2007 | WO | 2004035112 A2 | 4/2004 |
| EP | 1839690 | A1 | 10/2007 | WO | 2004045578 A2 | 6/2004 |
| EP | 1849488 | A1 | 10/2007 | WO | 2004045705 A2 | 6/2004 |
| EP | 1464347 | B1 | 1/2008 | WO | 2004055198 A2 | 7/2004 |
| EP | 1872810 | A1 | 1/2008 | WO | 2004073546 A2 | 9/2004 |
| EP | 1779878 | B1 | 4/2008 | WO | 2004073751 A2 | 9/2004 |
| EP | 1779879 | B1 | 4/2008 | WO | 2005092022 A2 | 10/2005 |
| EP | 1716828 | B1 | 5/2008 | WO | 2005092023 A2 | 10/2005 |
| EP | 1829568 | B1 | 6/2008 | WO | 2005092047 A2 | 10/2005 |
| EP | 1765190 | B1 | 7/2008 | WO | 2005104979 A1 | 11/2005 |
| EP | 1787606 | B1 | 8/2008 | WO | 2006026154 A2 | 3/2006 |
| EP | 1810702 | B1 | 10/2008 | WO | 2006044029 A2 | 4/2006 |
| EP | 1867349 | B1 | 11/2008 | WO | 2007001502 A2 | 1/2007 |
| EP | 2002812 | A1 | 12/2008 | WO | 2007001503 A2 | 1/2007 |
| EP | 1900347 | B1 | 4/2009 | WO | 2007100741 A2 | 9/2007 |
| EP | 1553902 | B1 | 5/2009 | WO | 2007109382 A2 | 9/2007 |
| EP | 2065020 | A1 | 6/2009 | WO | 2007109383 A2 | 9/2007 |
| EP | 1839689 | B1 | 8/2009 | WO | 2007109413 A2 | 9/2007 |
| EP | 1296732 | B1 | 11/2009 | WO | 2008011220 A2 | 1/2008 |
| EP | 1632210 | B1 | 12/2009 | WO | 2008036462 A2 | 3/2008 |
| EP | 1743670 | B1 | 1/2010 | WO | 2008055876 A1 | 5/2008 |
| EP | 1893251 | B1 | 1/2010 | WO | 2008046636 A3 | 6/2008 |
| EP | 2149359 | A1 | 2/2010 | WO | 2008088623 A2 | 7/2008 |
| EP | 2165725 | A1 | 3/2010 | WO | 2008115270 A2 | 9/2008 |
| EP | 1935440 | B1 | 4/2010 | WO | 2008117178 A2 | 10/2008 |
| EP | 2172235 | A1 | 4/2010 | WO | 2008147429 A1 | 12/2008 |
| EP | 1237608 | B2 | 5/2010 | WO | 2009000786 A2 | 12/2008 |
| EP | 2076232 | B1 | 5/2010 | WO | 2009089319 A1 | 7/2009 |
| EP | 1893250 | B1 | 6/2010 | WO | 2009117112 A2 | 9/2009 |
| EP | 1212111 | B1 | 7/2010 | WO | 2009120184 A2 | 10/2009 |
| EP | 1996249 | B1 | 9/2010 | WO | 2009140185 A1 | 11/2009 |
| EP | 1996269 | B1 | 9/2010 | WO | 2009145799 A1 | 12/2009 |
| EP | 2065001 | B1 | 10/2010 | WO | 2010008424 A2 | 1/2010 |
| EP | 1913926 | B1 | 12/2010 | WO | 2010030528 A2 | 3/2010 |
| EP | 1960041 | B1 | 12/2010 | WO | 2010056448 A1 | 5/2010 |
| EP | 1726323 | B1 | 2/2011 | WO | 2010081838 A2 | 7/2010 |
| GB | 2012373 | A | 7/1979 | WO | 2010088143 A1 | 8/2010 |
| WO | 9315777 | A2 | 8/1993 | WO | 2010088144 A1 | 8/2010 |
| WO | 9319791 | A1 | 10/1993 | WO | 2010129128 A1 | 11/2010 |
| WO | 9626701 | A1 | 9/1996 | | | |
| WO | 9716169 | A1 | 5/1997 | | | |

\* cited by examiner

FEEDING SET FOR A PERISTALTIC PUMP SYSTEM

FIELD

The present disclosure relates generally to enteral feeding apparatus, a feeding set for such an apparatus, and a method of connecting the feeding set to the apparatus.

BACKGROUND

Currently, there are many different types of nasogastric, esophagastric, and abdominal feeding apparatus for supplying nutritional products to patients. These nutritional products, which are almost always flowable, are available for a variety of supplanting and supplemental feeding requirements. For example, a number of suitable nutritional products are available from Abbott Nutrition and sold under the following registered trademarks: GLUCERNA; JEVITY; JUVEN; NEPRO; OPTIMENTAL; OSMOLITE; OXEPA; PERATIVE; PROMOTE; PULMOCARE; SUPLENA; TWOCAL; and VITAL.

Conventional feeding apparatus typically include a pump and various components and/or accessories for transferring the nutritional product from a container (e.g., a bottle) to the patient. These components, which may be reusable or disposable, typically include various tubing and connectors. All of the components (e.g., tubing and connectors) necessary for transferring the nutritional product to a patient using a specific pump are often collectively referred to as a "feeding set".

The feeding sets for these feeding apparatus are often manufacturer-specific and sometimes even model specific. That is, the feeding sets are often designed by a particular manufacturer for exclusive use with its pumps or one of its pump models and cannot be used with a pump made by another pump manufacturer. Thus, the feeding sets can vary across the industry and between manufacturers.

The prevalence of such nutritional products, pumps, and feeding sets has established large manufacturing volumes across the industry, which has lead to new inquiries seeking improved manufacturing techniques, lower costs, and easier to use capabilities for health care and nutritional care providers. Many attempts have already been made to improve the state of the art, but many deficiencies continue to be found in the current technology.

Several particularly troublesome issues associated with the use of feeding sets stand out. One issue that continues to vex providers is that most present-day feeding sets are susceptible to leaking nutritional product during initial setup and post-feeding breakdown of the feeding set. To correct this problem, many innovators in the art have attempted to incorporate valves into their feeding sets.

While various types of valves have been found to be effective in some circumstances, the presently known valve technologies present added issues and challenges. Such valves increase manufacturing costs, fabrication time, and in many instances also decrease ease-of-use. In most instances, the prior technologies require multiple hands to actuate the valve. Other valve arrangements are difficult to prime or initiate flow through the enteral feeding apparatus.

Moreover, in order to accurately control the feed rate (i.e., the rate at which the nutritional product is delivered by the pump, through the feeding set and into the patient), at least some of the components of the feeding set must be securely held in place relative to other components of the pump, such as a rotor of the pump. In many pump designs, and particularly conventional peristaltic pump designs one or more components of the feeding set (e.g., a cassette or peristaltic tubing) are held in place by a door that closes over the respective components. If the door is damaged or misaligned, the positioning of the feeding set components relative to the pump can change. This relative movement adversely effects the accuracy of the feed rate. Thus, if the door is open, misaligned and/or damaged, the pump will not operate or will not do so properly. Moreover, any misalignment or damage to the door may also adversely effect any sensors (e.g., pressure sensors, air-in-line sensors) associated with the operation of the pump.

Unfortunately, the doors on many conventional pumps are easily susceptible to damage. Many past attempts to ensure that the proper feed rate is maintained have included incorporating in-line occlude actuators into the door. If the door does not close or remain closed properly, the feeding set is occluded to prevent the nutritional product from being pumped. It is desirable, however, if the operation of the pump is not dependent on the proper alignment and operation of the door of the pump.

SUMMARY

In one aspect, a feeding set for a peristaltic pump system generally comprises a cassette configured for releasable connection to the pump system. A deflectable lumen priming actuator is formed integrally with the cassette for conjoint connection to and disconnection from the pump system with the cassette as a single unit. The priming actuator includes an actuation pad and is moveable from a rest position to a deflected position. A substantially flexible lumen is coupled to the cassette. The lumen has an inlet, an outlet, and an extensible peristalsis loop. An inline valve is received within the lumen and is arranged to obstruct fluid flow through the lumen. The actuation pad of the priming actuator is located proximate the inline valve in the rest position and is adapted to contact and apply a force to the lumen adjacent the inline valve when the priming actuator is moved to the deflected position. The force applied to the lumen is sufficient to establish at least one flow channel between the inline valve and the lumen.

In another aspect, a feeding set for a peristaltic pump system generally comprises a cassette configured for releasable connection to the pump system. A priming actuator is formed integral with the cassette for conjoint connection to and disconnection from the pump system with the cassette as a single unit. The priming actuator is configured to be manually actuated from a rest position to a deflected position. A lumen is coupled to the cassette. The lumen has an inlet, an outlet, and an extensible peristalsis loop. An inline valve is received within and substantially obstructs fluid flow within the lumen. When the priming actuator is manually actuated to the deflected position, the priming actuator acts on the lumen to thereby deform the lumen adjacent the inline valve to establish a fluid channel between the lumen and the inline valve.

In still another aspect, a feeding set for a peristaltic pump system having a rotor and a retainer generally comprises a cassette adapted for engagement with the retainer of the pump system. The cassette has a priming actuator formed integrally therewith. The priming actuator is moveable between a rest position and a deflected position. The priming actuator includes a flexure arm and an actuation pad extending outward from the flexure arm. A lumen is coupled to the cassette and has an inlet, an outlet, and an extensible peristalsis loop. The peristalsis loop is confirmation for placement about the rotor. An inline valve is received within the lumen and arranged to obstruct fluid flow within the lumen. The actuation pad of the priming actuator is disposed adjacent the inline valve in the rest position of the priming actuator and is moved into direction contact with the lumen adjacent the inline valve when the priming actuator is moved to the deflected position to establish at least one flow channel between the inline valve and the lumen.

DETAILED DESCRIPTION OF THE DRAWINGS

Figure 1:
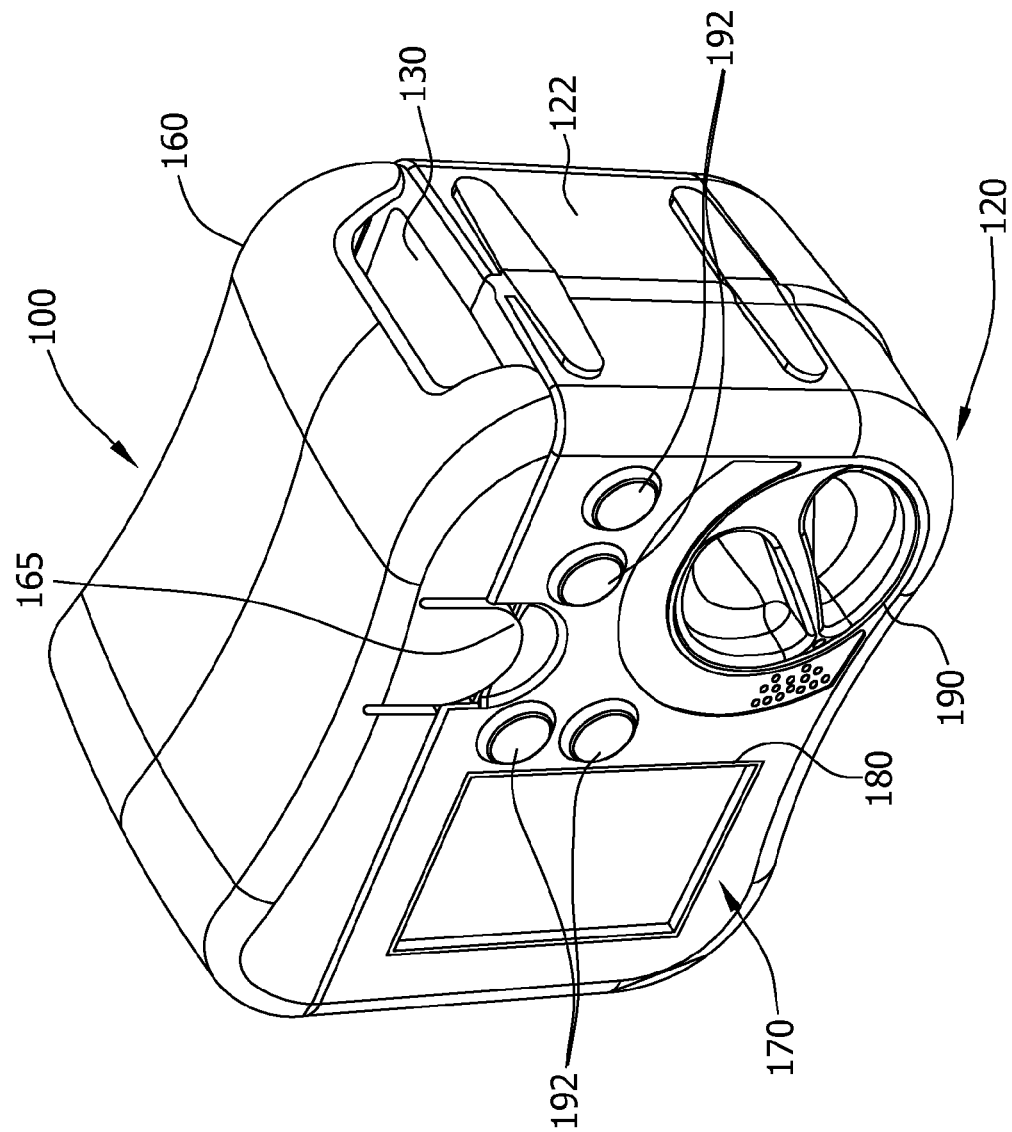
FIG. 1 is a perspective of one embodiment of an enteral feeding apparatus.
Figure 2:
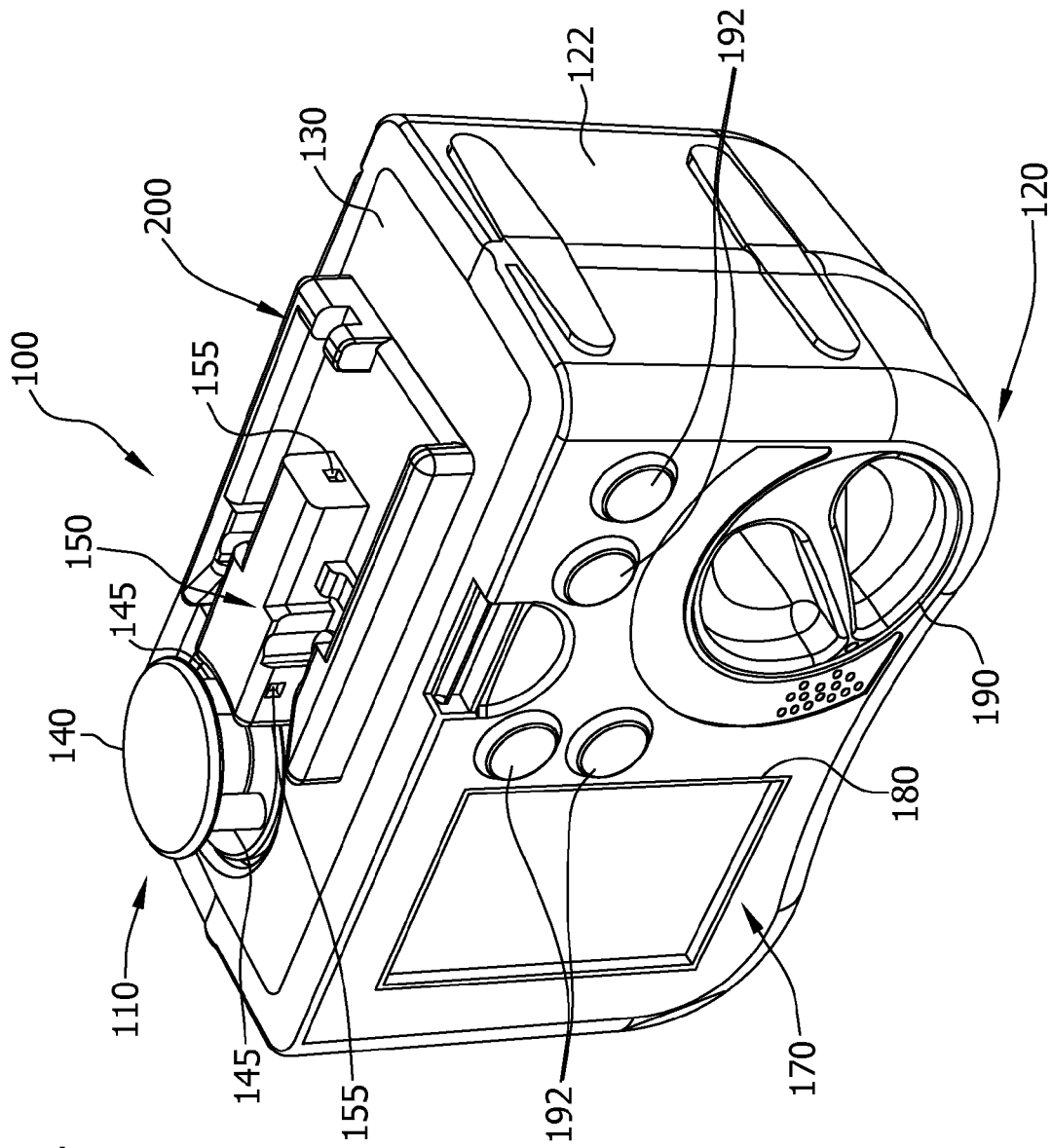
FIG. 2 is a perspective of the apparatus of FIG. 1 with a door of the apparatus removed to illustrate a peristaltic pump system of the apparatus.
Figure 3:
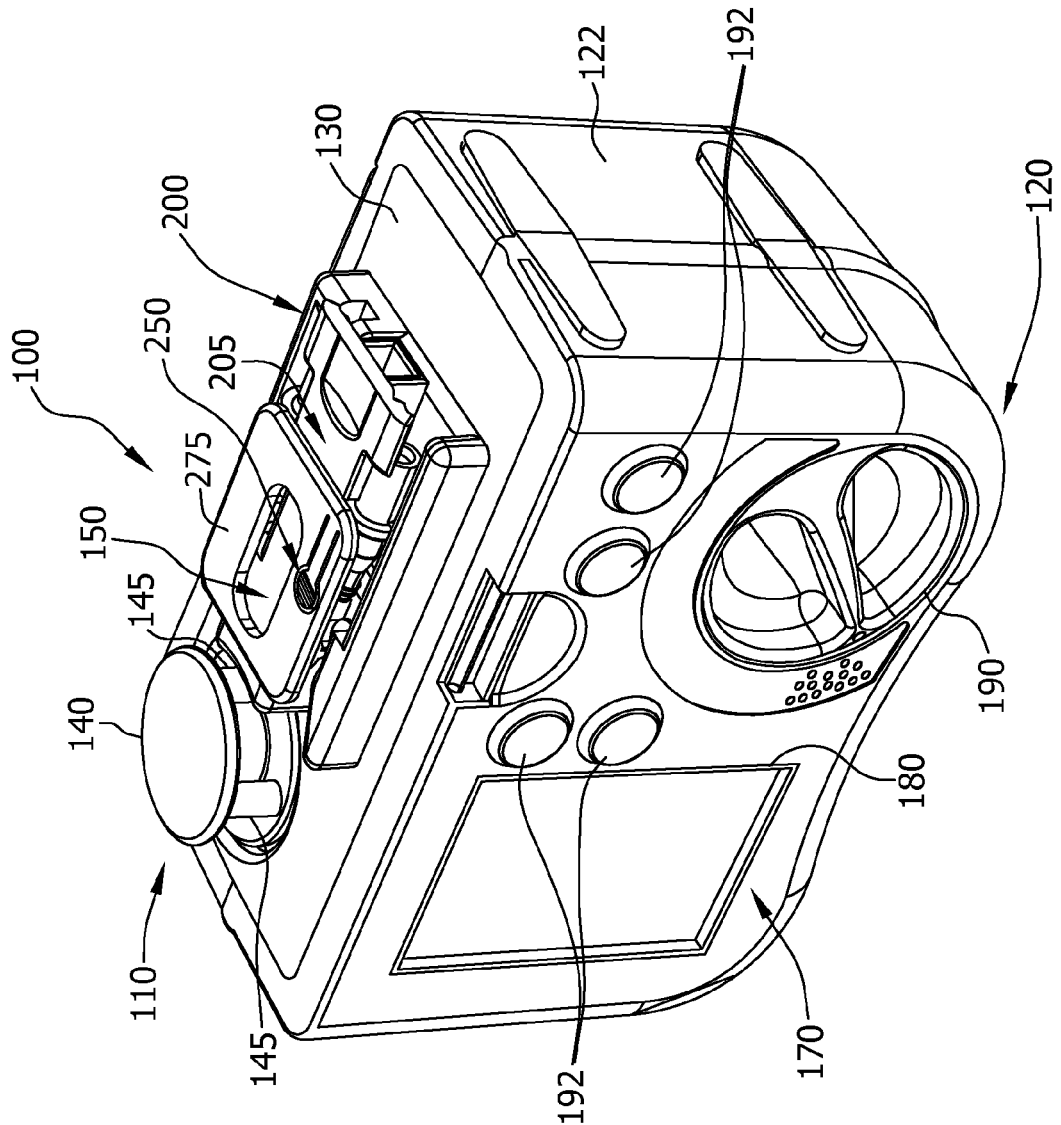
FIG. 3 is a perspective of the apparatus of FIG. 2 with a cassette of a feeding set releasably engaged to the pump system.

With reference to FIGS. 1-3, an enteral feeding apparatus, indicated generally at 100, is illustrated therein. The enteral feeding apparatus 100 includes a pump system, indicated generally at 110, mounted on a base, indicated generally at 120 (FIGS. 2 and 3). A door 160 (broadly, "a closure") of the enteral feeding apparatus 100 is provided to selectively cover and uncover the pump system 110 (FIG. 1). In the illustrated embodiment, the door 160 is selectively removable from the base 120 via a plurality of releasable latches 165 (only one of the releasable latches being illustrated in FIG. 1). In FIG. 1, the door 160 is illustrated in its closed position covering the pump system 110 and, in FIGS. 2 and 3, in its opened position (i.e., removed) thereby exposing the pump system 110. In the illustrated embodiment, the door 160 is completely removable from the base when in its opened position but it is understood that the door 160 could be partially removable from the base 120, such as by mounting the door to the base using a hinged connection. It is further understood that the door 160 can be omitted from the enteral feeding apparatus 100.

As seen in FIGS. 2 and 3, the illustrated pump system 110 is suitably a peristaltic pump system including a platen 130 mounted to the base 120 for carrying a rotor 140 (broadly, a "bearing surface") and a retainer, indicated generally at 150. The rotor 140 of the pump system 110 has at least one peristalsis inducing roller 145 and, in the illustrated embodiment, has three peristalsis inducing rollers (two of the rollers being illustrated in FIGS. 2 and 3).

The retainer 150 is mounted on the platen 130 generally adjacent the rotor 140 and includes at least one engagement member (or, in this embodiment, three recesses 155) that enables the pump system 110 to capture and thereby positively secure a cassette, indicated generally at 205, to the pump system 110. Two of the recesses 155 are located on sidewalls of the retainer 150 and one of the recesses is located on a back wall of the retainer. The interconnection between the recesses 155 of the retainer 150 and the cassette 205 is described in more detail below.

With reference again to FIG. 1, the base 120 of the enteral feeding apparatus 100 includes a housing 122, a pump controller 170, and a user display interface 180. In the illustrated configuration, the user display interface 180 has a touch-sensitive screen for allowing a user to operate the controller 170. In another configuration, the controller 170 can be remotely operated using Wi-Fi, Bluetooth®, and/or other types of wireless computer communications capabilities. Remote operation of the controller 170 can be used to replace or in conjunction with the user display interface 180. The illustrated enteral feeding apparatus 100 also includes actuators such as a rotary knob 190 and a plurality of buttons 192 for operating various aspects of the controller 170.

Figure 9:
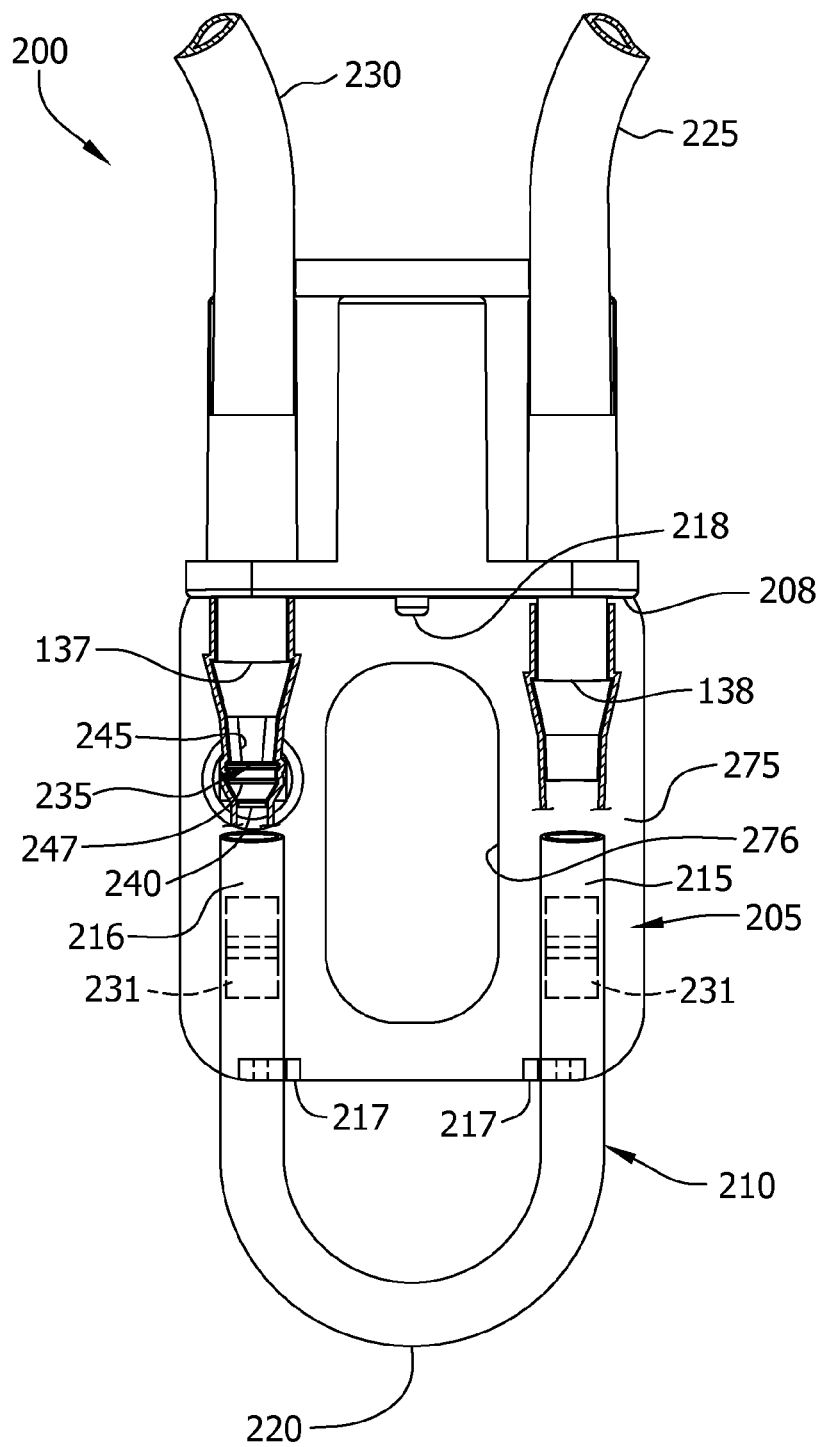
FIG. 9 is a plan view of the feeding set including the cassette and a lumen attached to the cassette.
Figure 10:
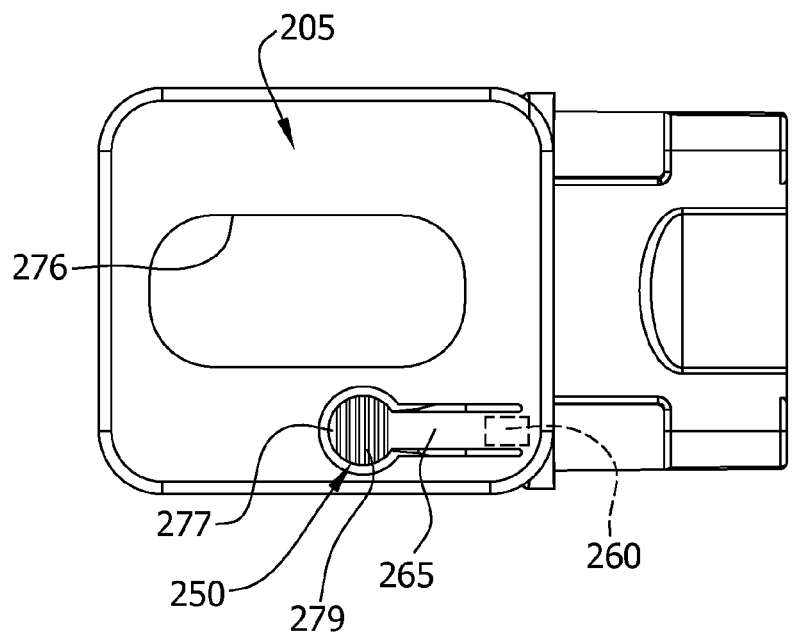
FIG. 10 is a top plan view of the cassette.
Figure 11:
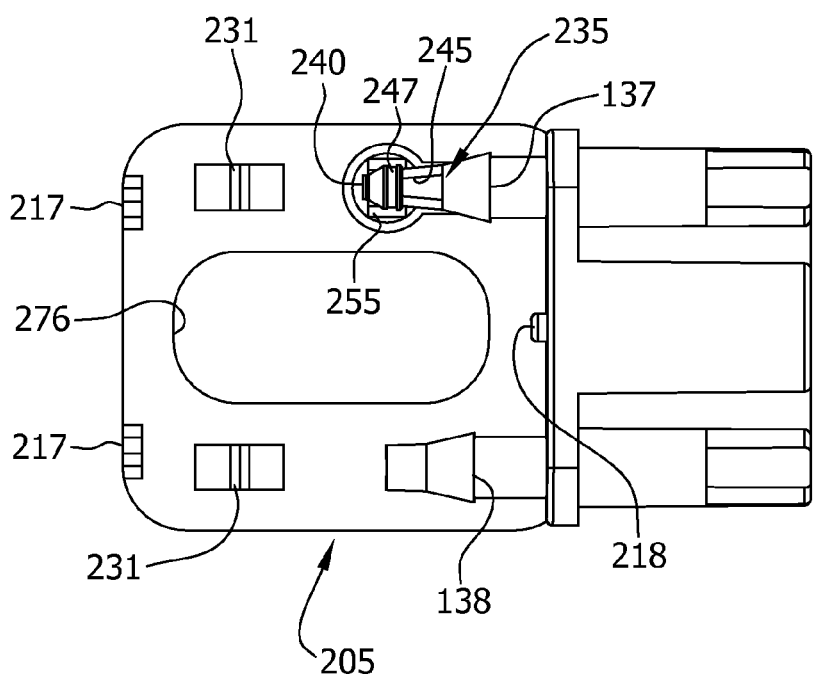
FIG. 11 is a bottom plan view of the cassette.
Figure 12:
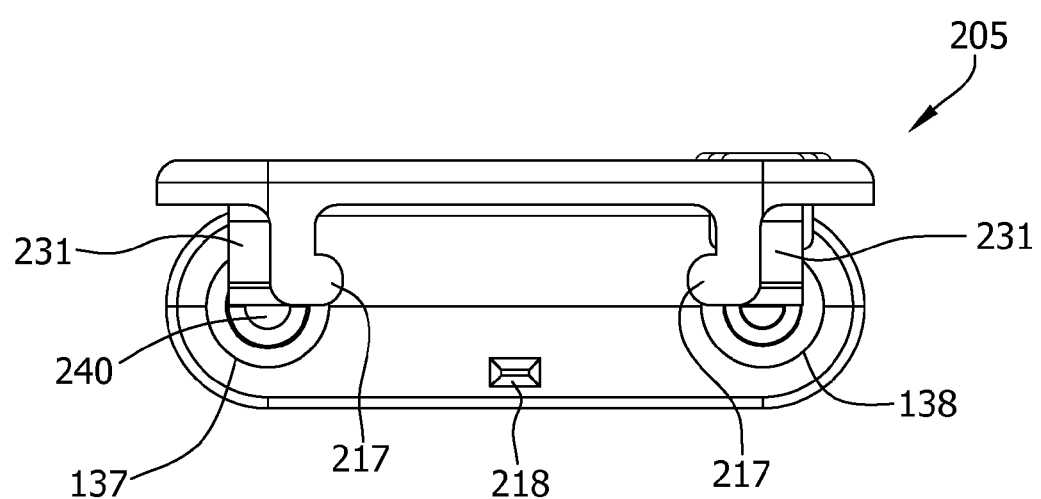
FIGS. 12 and 13 are front and back end views, respectively, of the cassette.
Figure 13:
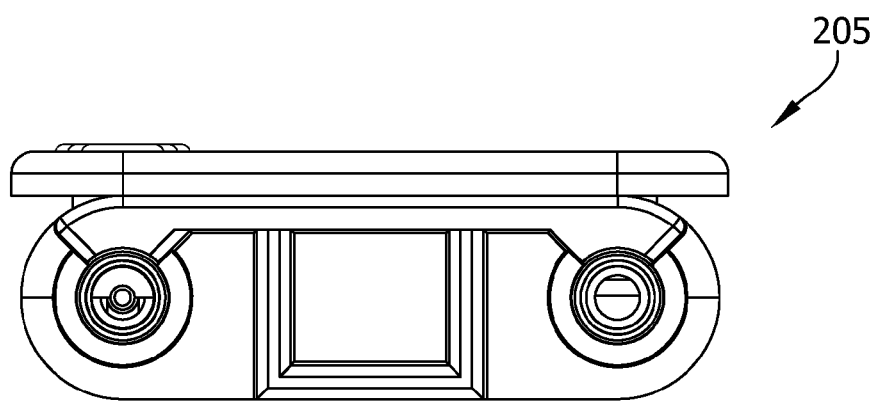
Figure 18:
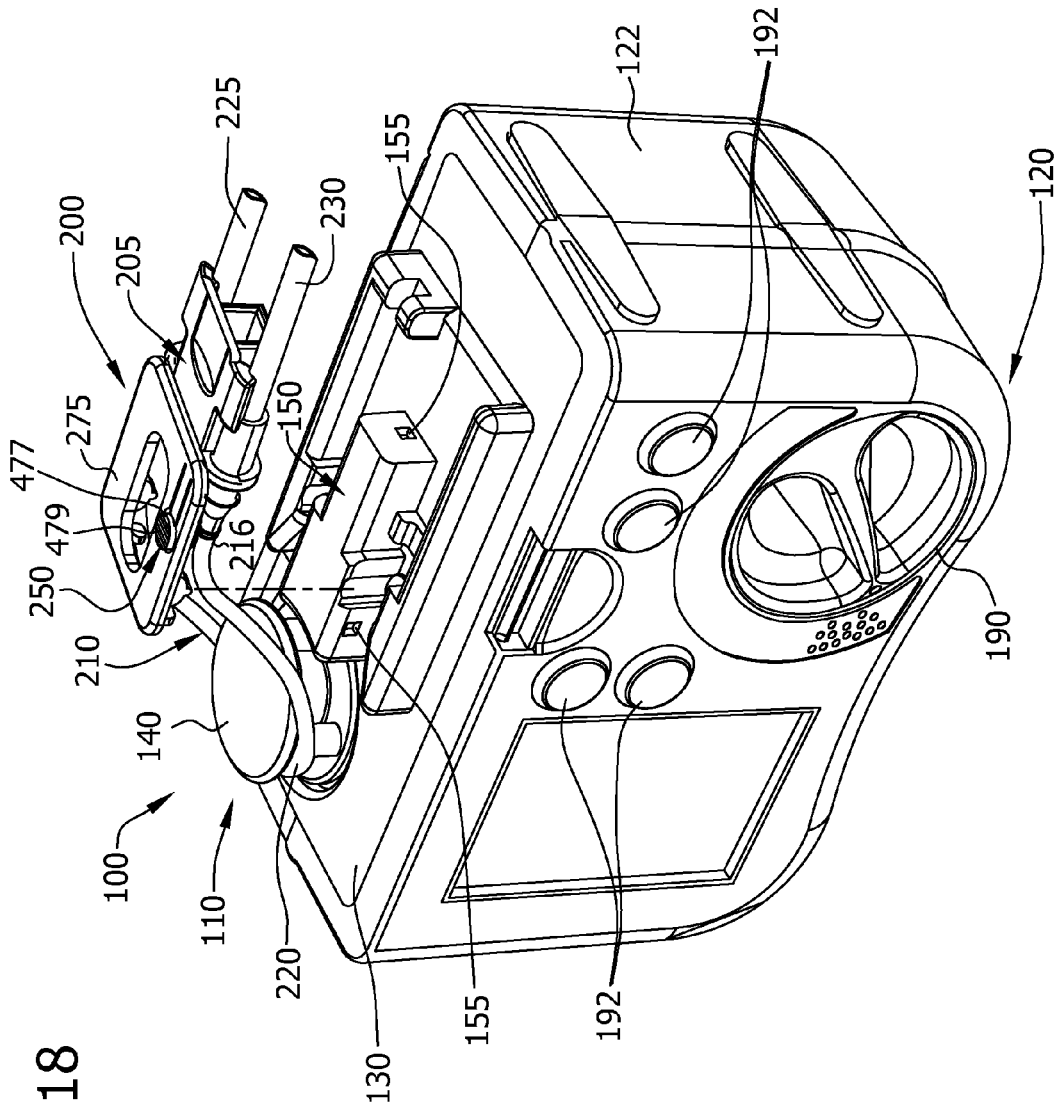
FIG. 18 is perceptive of the enteral feeding apparatus illustrating the feeding set in the process of being releasably engaged to the pump system.

As illustrated in FIGS. 9 and 18, the enteral feeding apparatus 100 comprises a feeding set, indicated generally at 200. The illustrated feeding set 200 includes the cassette 205 and a substantially flexible lumen, indicated generally at 210, coupled to the cassette 205. In one suitable embodiment, the lumen 210 has a friction fit with the cassette 205. In the illustrated embodiment, for example, the cassette 205 includes a pair of barbs 137, 138 for receiving ends of the lumen 210 (FIG. 9). It is understood, however, that other suitable connectors can be used to couple the lumen 210 to the cassette 205.

The feeding set 200 illustrated in the accompanying drawings is adapted for single-use. That is, the feeding set 200 is designed to be used once, removed from the pump system 110, and then disposed of.

The lumen 210 can be formed from any suitable polymeric materials, which include for example, silicone and/or other suitable elastomers, polytetrafluoroethylene (PTFE), polyvinyl chloride (PVC), and similar materials and combinations thereof. In one suitable embodiment, the polymeric material used to make the lumen 210 has a Shore durometer rating between about and about 50 Shore O-scale and between about 10 and about 85 Shore A-scale. More preferably, the lumen 210 has a Shore durometer rating of at least 30. In one suitable embodiment, the lumen 210 has a Shore durometer rating in a range between about 45 and about 85 and more preferably between about 45 and about 65 on the Shore A-scale. In another suitable embodiment, the lumen 210 has a Shore durometer rating in a range between about 60 and about 80 on the Shore A-scale.

As seen in FIG. 9, the lumen 210 defines an extensible peristalsis loop 220 having two ends (i.e., an inlet end 215 and an outlet end 216) that are connected to the cassette 205. More specifically and as explained above, the ends 215, 216 of the lumen 210 are connected to the barbs 137, 138 formed on the cassette 205. Tubing 225, 230 also extends from the cassette 205 to form an inlet and an outlet, respectively, of the feeding set 200. As illustrated in FIG. 18, the extensible peristalsis loop 220 is tensioned about the rotor 140 when the cassette 205 is engaged with the pump system 110.

In one embodiment, the cassette 205 is made from a durable polymeric material selected from a group that includes, for example, polypropylenes, polystyrenes, nylons, high-density polyethylenes, polycarbonates, acrylics, and similar polymeric materials. In a suitable embodiment, the cassette 205 is formed from such polymeric materials to have a hardness rating on the Shore durometer scale that is approximately equal to or greater than about 85-95 on the Shore A-scale and/or about 40 to about 50 on the Shore O-scale.

In the illustrated embodiment, the cassette 205 of the feeding set 200 has an inline valve, indicated generally at 235, that is adapted to be received within the lumen 210 (FIG. 9). The inline valve 235 is made from a material that has a hardness rating that is approximate equal to or more rigid than the material used to make the lumen 210. In one suitable embodiment, the lumen 210 is more flexible, more stretchable, and/or more ductile than the inline valve 235 thereby creating a relative material hardness, rigidity, and/or deformability differential between lumen 210 and inline valve 235. As a result, the lumen 210 can be easily stretched, flexed, or deformed without a corresponding deflection, deformation, or flexure of the inline valve 235.

Figure 6:
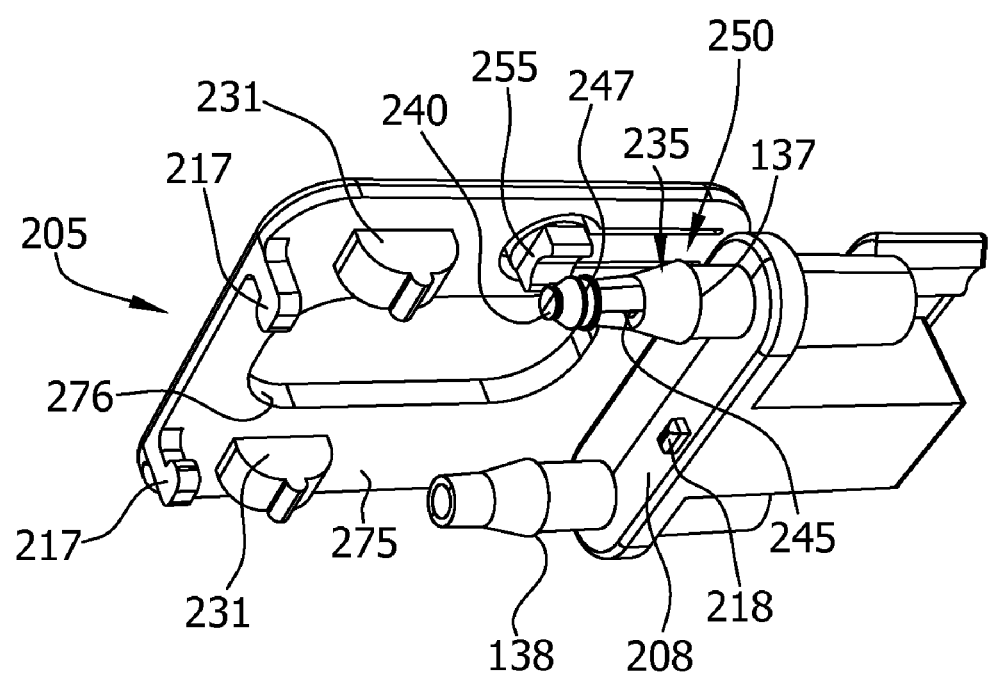
FIG. 6 is a bottom side perspective of the cassette of FIGS. 3 and 5.
Figure 7:
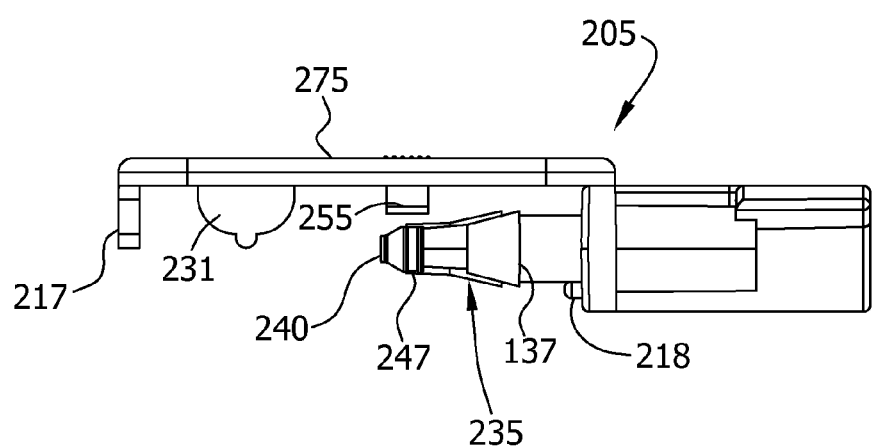
FIG. 7 is a right-side elevation of the cassette rotated from the view shown in FIG. 6.
Figure 8:
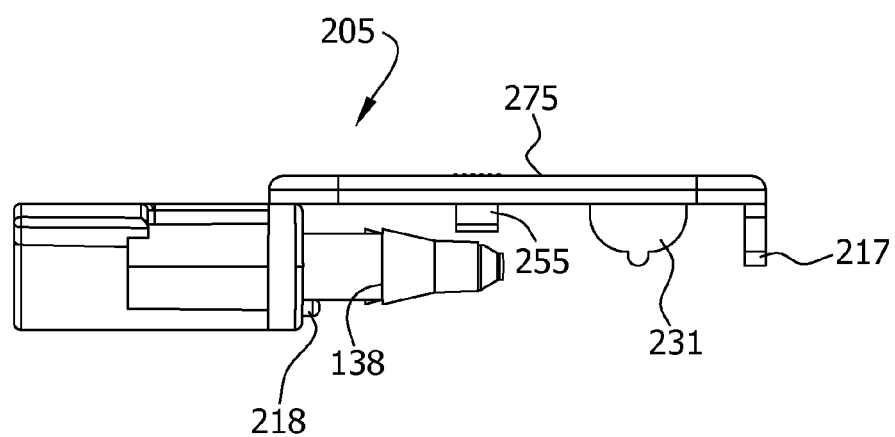
FIG. 8 is a left-side elevation of the cassette.

As seen in FIGS. 6 and 7, the inline valve 235 is formed as one-piece with one of the barbs 137 of the cassette 205, and the outlet end 216 of the lumen 210 is received thereon. The inlet end 215 of the lumen is received on the other barb 138 of the cassette 205 (FIG. 9). It is contemplated that the barbs 137, 138 of the cassette 205 can be omitted. In such an embodiment, the inline valve 235 can be formed as a discrete component that can be inserted into the lumen 210.

Figure 14:
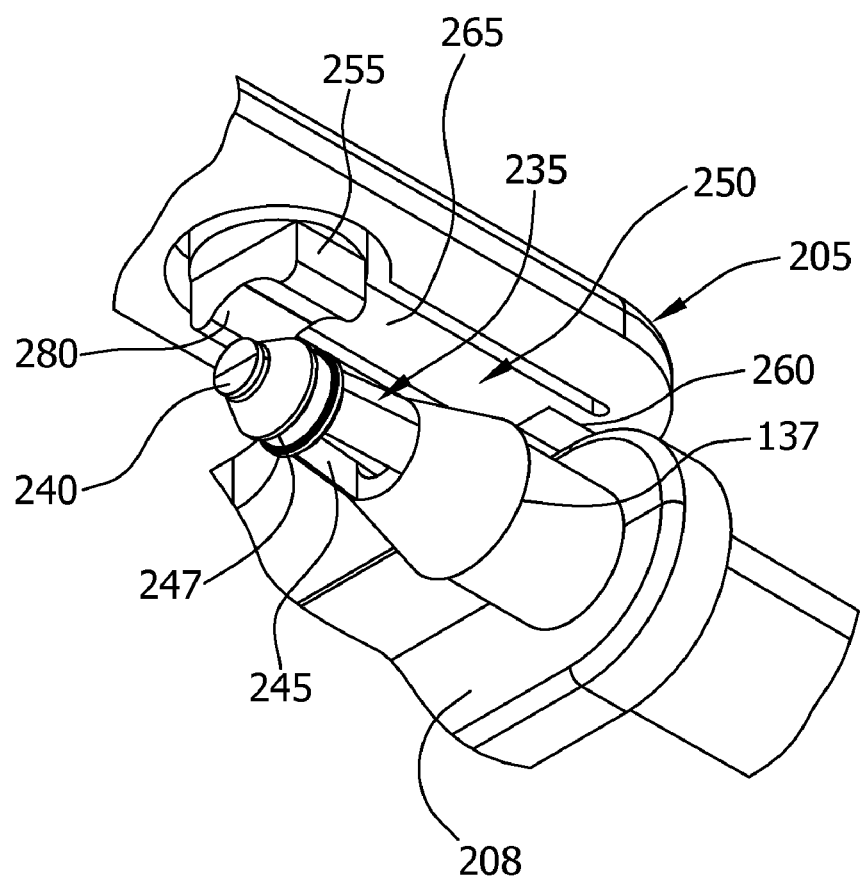
FIG. 14 is an enlarged fragmentary perspective of a portion of the cassette.
Figure 15:
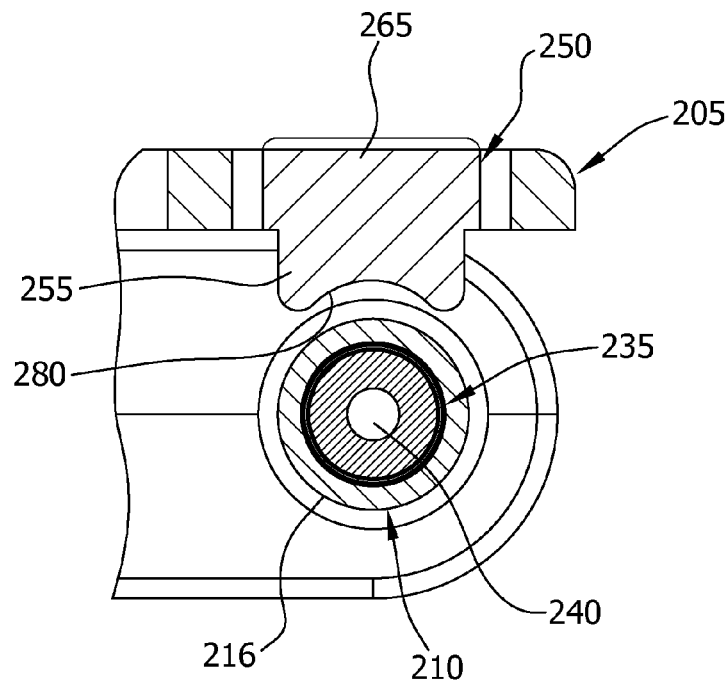
FIG. 15 is an end view of the portion of the cassette illustrated in FIG. 14 with the lumen of the feeding set attached thereto.
Figure 16:
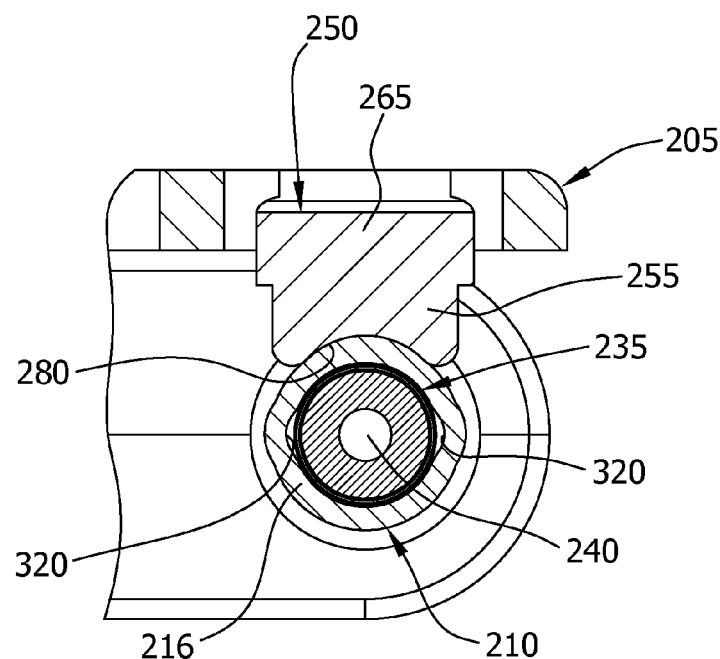
FIG. 16 is an end view similar to FIG. 15 but with a primer of the cassette being deflected and acting on the lumen.

With reference to FIGS. 14-16, the inline valve 235 has a luminal plug 240 received within the lumen 210 that nominally occludes fluid communication through the lumen 210. The inline valve 235 also includes at least one valve port 245 that is formed in a sidewall of the inline valve. The valve port 245 is nominally sealed from fluid communication by the sidewalls of the lumen 210 being sealingly stretched about a sealing periphery 247 of the luminal plug 240 when the associated barb 137 is received within the lumen.

Figure 5:
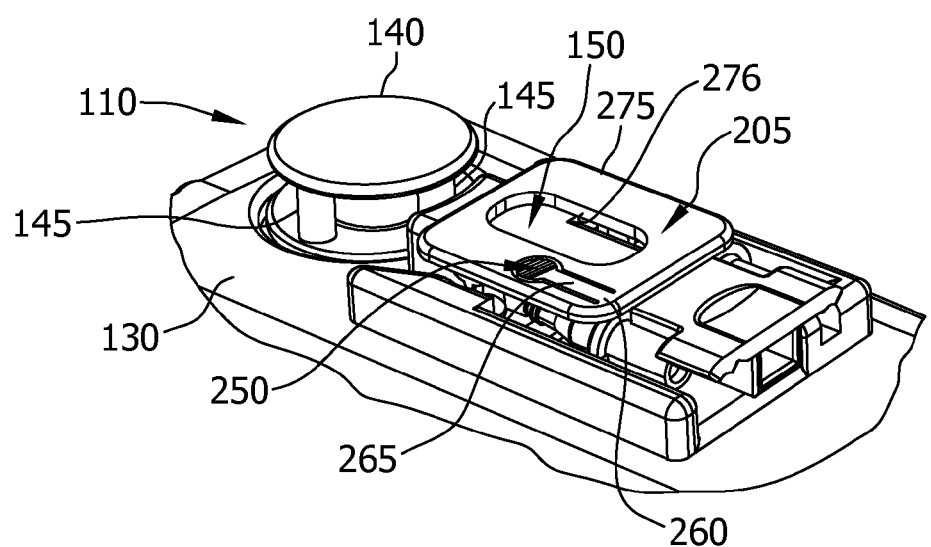
FIG. 5 is an enlarged fragmentary perspective illustrating the cassette releasably engaged to the pump system of the apparatus of FIG. 3.

As seen in FIGS. 3, 5 and 6, the cassette 205 also includes a deflectable lumen priming actuator, indicated generally at 250. The priming actuator 250 has a flex joint 260, a flexure arm 265 extending outward from the flex joint, and an actuation pad 255 formed on the flexure arm at a location spaced from the flex joint. As seen in FIG. 14, the actuation pad 255 of the priming actuator 250 is positioned proximate the inline valve 235. The actuation pad 255 comprises an arcuate outer surface 280 that is selected to be complementary to the shape of the lumen 210 (FIG. 16). In the illustrated embodiment, the lumen priming actuator 250 is formed integrally with the cassette 205. That is, the lumen priming actuator 250 and the cassette 205 can be formed together as a single-piece (e.g., by being molded together) or can be formed separately and permanently secured together, such as by adhesive, thermal bonding, welding or other suitable techniques. As a result, the priming actuator 250 and the cassette 205 are attachable to and removable from the pump system 110 as a single-unit.

In the illustrated embodiment and as seen in FIG. 6, the priming actuator 250 is disposed above the inline valve 235. But it is understood that the priming actuator 250 can be disposed at any position about the circumference of the inline valve 235. For example, the priming actuator 250 can be disposed adjacent one of the sides of the inline valve 235 or can be disposed beneath the inline valve without departing from the scope of this invention.

The priming actuator 250 can be actuated from a rest position as shown in FIG. 15 to a deflected or actuated position as shown in FIG. 16. In the deflected or actuated position of FIG. 16, the flexure arm 265 is pivoted about the flex joint 260 so that the actuation pad 255 is urged into contact with the lumen 210. The lumen 210 is thereby sandwiched between the actuation pad 255 and the sealing periphery 247 of the inline valve 235 to establish at least one flow channel 320 (FIG. 16). The at least one flow channel 320 enables fluid communication between the inlet tubing 225 and outlet tubing 230 through the valve port 245 of the inline valve 235 of the cassette 205. As seen in FIG. 16, the lumen 210 is pushed against the sealing periphery 247 of the inline valve 235 by the actuation pad 255, which stretches or otherwise deforms portions of the lumen 210 to form the at least one flow channel 320 (two flow channels being illustrated in FIG. 16).

While the inline valve 235 is illustrated to be between the peristalsis loop 220 and the outlet tubing 230, it is contemplated that the inline valve can be disposed between the peristalsis loop 220 and the inlet tubing 225.

The cassette 205 further includes a generally planer upper wall 275 with an opening 276 therein. It is understood, however, that the opening 276 can be omitted. A pair of latching clips 217 extends downward from the upper wall 275. In the illustrated embodiment, the clips 217 are adjacent an outer free edge of the upper wall 275. It is understood that the clips 217 can have different locations on the cassette 205. A pair of alignment members 231 is disposed on an underside of the planer upper wall 275 and extends downward therefrom. As seen in FIG. 6, a generally vertical wall 208 of the cassette 205 extends downward from the upper wall 275. A projection or nub 218 and the two barbs 137, 138 are disposed on and extend outward from the vertical wall 208.

Figure 17:
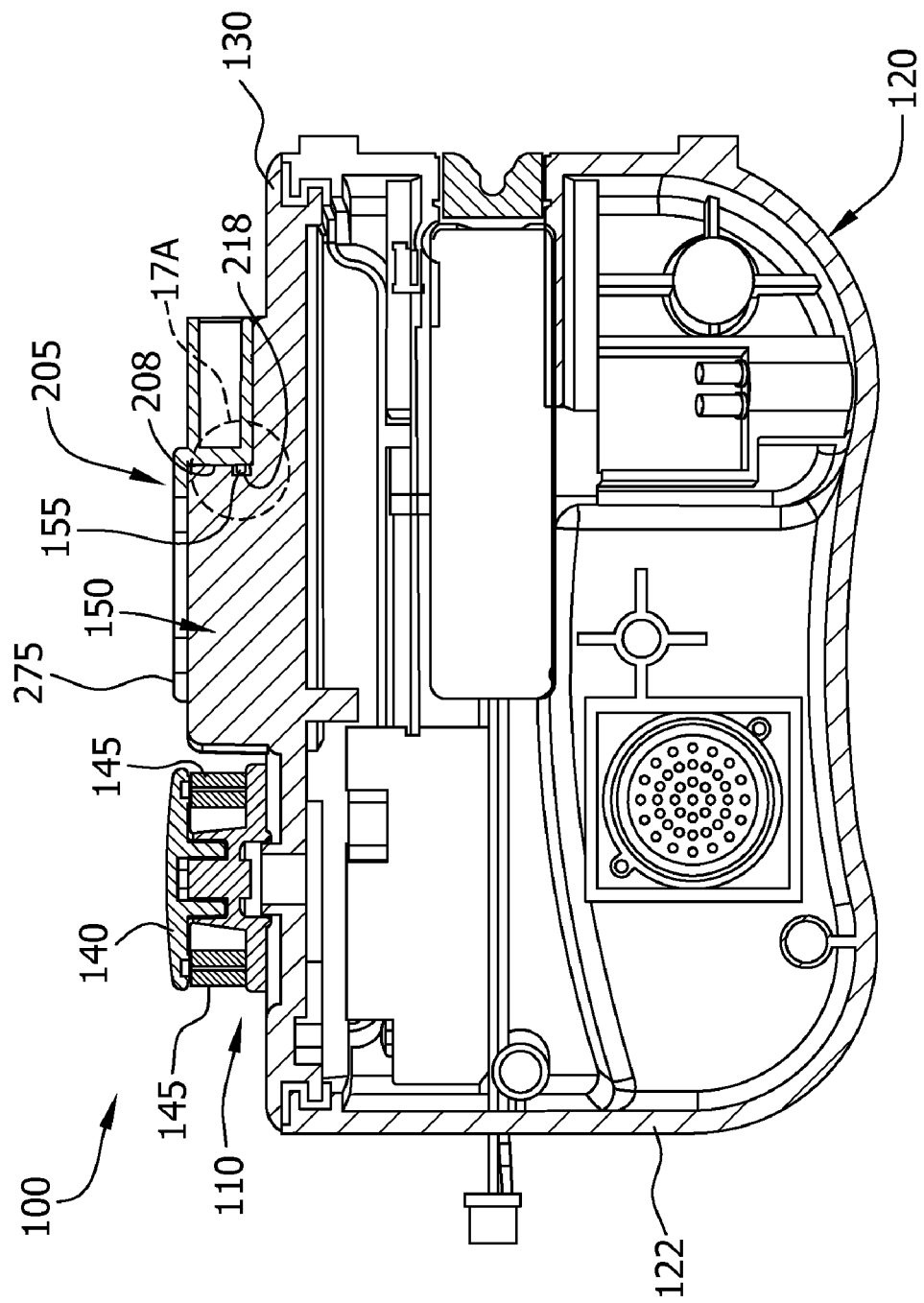
FIG. 17 is a vertical cross-section of the enteral feeding apparatus illustrated in FIG. 3 with the cassette of the feeding set releasably engaged thereto.
Figure 17A:
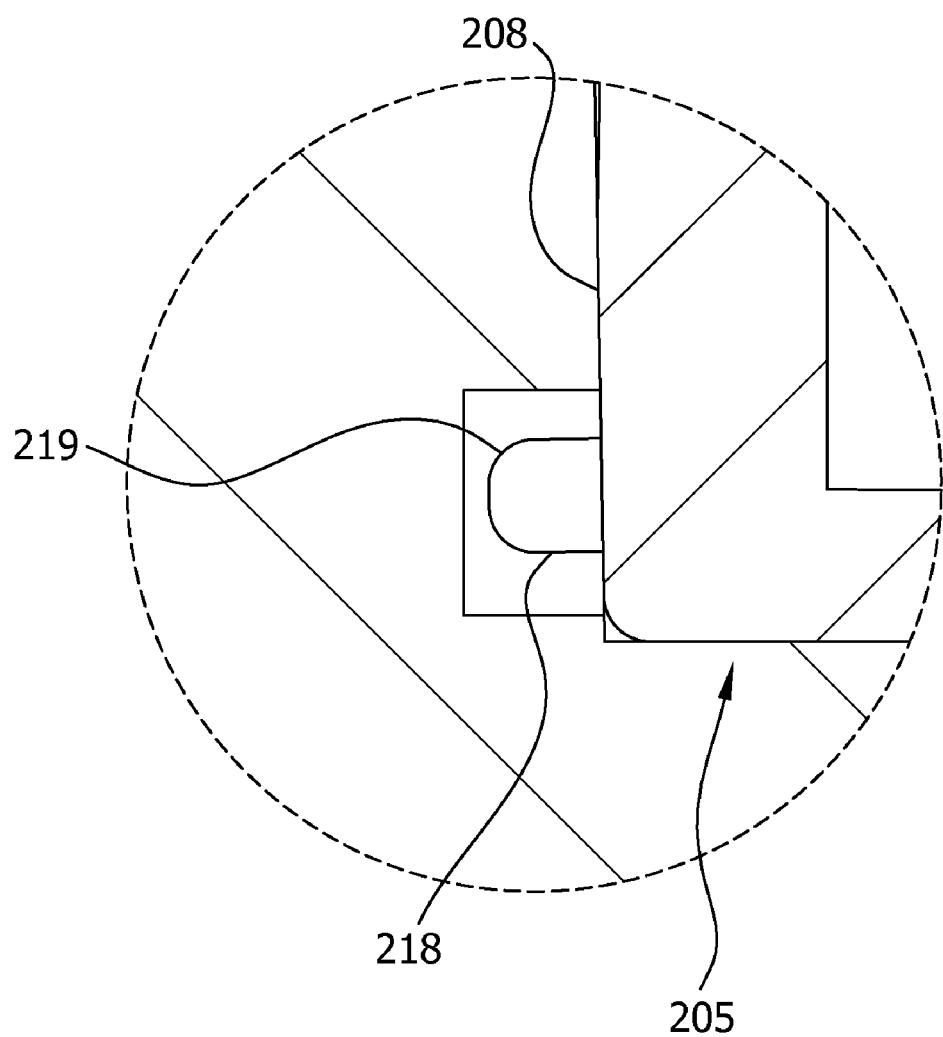
FIG. 17a is an enlarged cross-section of the cassette of FIG. 17 illustrating a nub, or projection of the cassette.

The recesses 155 in the retainer 150 are suitably positioned to cooperate with latching clips 217 and the projection 218 (broadly, an engagement member). More specifically, the recesses 155 on the sidewall of the retainer and the latching clips 217 cooperate to provide a snap-fit connection between the retainer 150 and the cassette 150. These recesses 155 and the latching clips 217 enable haptically functional tactile feedback to users such that the cassette 205 can be snapped into place on the pump system 110 and thereupon emit acoustical and vibrational feedback to a user during operation. Thus, the tactile feedback provides both a visual and audio cue to the user that the cassette 205 is properly secured to the retainer 150. The recess 155 in the back wall of the retainer 150 is suitably located to receive the projection 218 located on the vertical wall 208 of the cassette 205. As illustrated in FIG. 17A, the projection 218 is suitably sloped, or angled, and in the illustrated embodiment is slightly rounded, along at least a portion of a front surface 219 to facilitate movement of the projection into and/or outward from the recess 155 in the back wall of the retainer 150.

FIG. 18 illustrates the cassette 205 in the process of being engaged with the pump system 110. As seen therein, the peristalsis loop 220 of the lumen 210 is looped around the rotor 140 of the pump system 110. The lumen 210 is then stretched by pulling the cassette 205 away from the rotor 140. The cassette 205 is pushed downward and into contact with the retainer 150 of the pump system 110. More specifically, the latching clips 217 of the cassette 205 are engaged via a snap-fit with the recesses 155 in the sidewall of the retainer 150. The projection 218 on the vertical wall 208 of the cassette 205 is received within the recess 155 in the back wall of the retainer 150 (FIG. 17). It is contemplated that, in some embodiments, the latching clips 217 can be omitted. In these embodiments, the projection 218 on the vertical wall 208 of the cassette 205 being received within the recess 155 in the back wall of the retainer 150 would provide positive connection between the cassette and the pumping system 110.

The tension in the lumen 210 biases (i.e., urges or pulls) the cassette 205 toward the rotor 140. As a result, the lumen 210 biases (i.e., urges or pulls) the vertical wall 208 of the cassette 205 against the back wall of the retainer 150 thereby holding the projection 218 within the recess 155. The projection 218 thus inhibits the cassette against upward movement relative to the pump, i.e., to inhibit the cassette against inadvertent disconnection from the pump. In one suitable embodiment, the lumen 210 holds the vertical wall 208 of the cassette 205 against the back wall of the retainer 150 with about 4 pounds of tensile force. It is contemplated, however, that the lumen 210 material and dimensions may be selected to provide more or less tensile force without departing from the scope of this invention.

Figure 19:
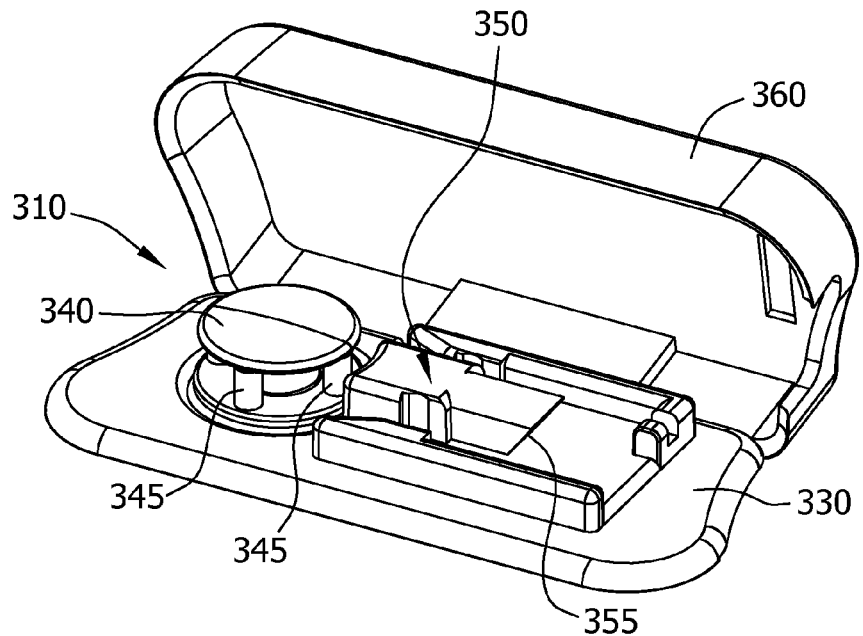
FIG. 19 is a perspective of another embodiment of a pump system for use with the apparatus.
Figure 22:
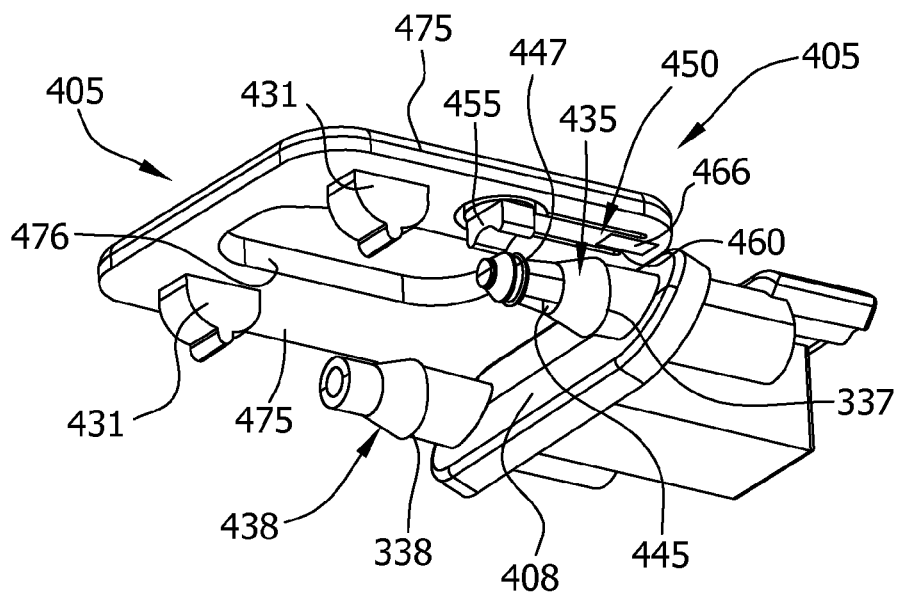
FIG. 22 is a bottom side perspective of the cassette removed from the pump system.
Figure 23:
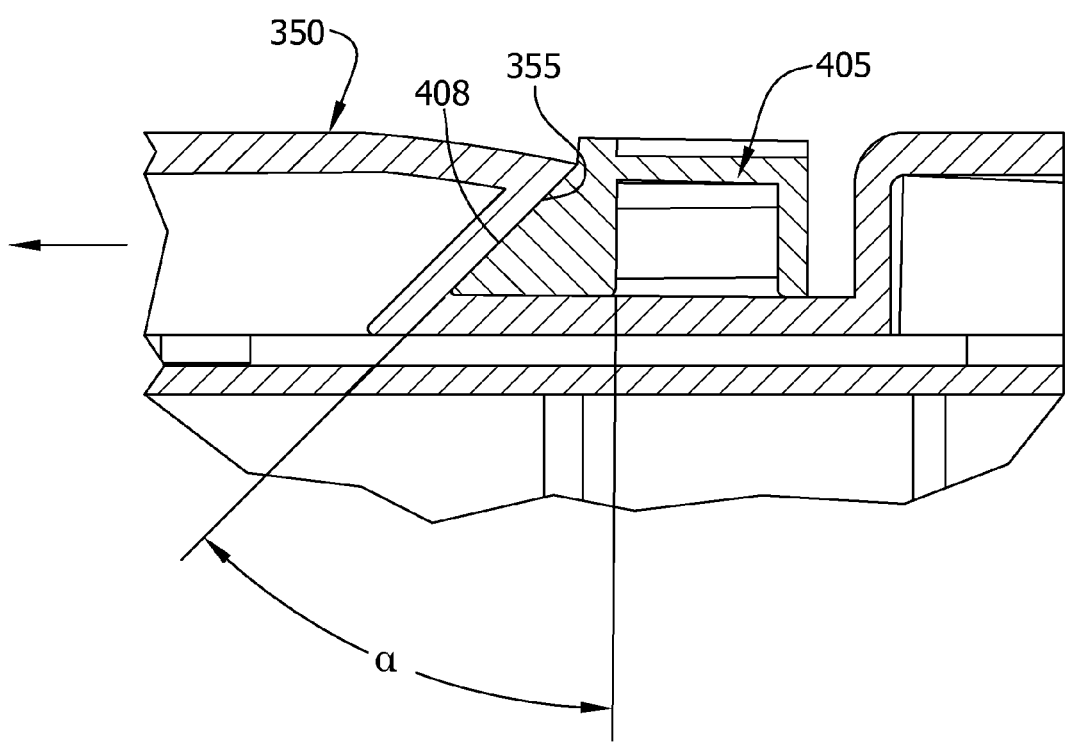
FIG. 23 is an enlarged fragmentary view of the cross-section of FIG. 20 showing the cassette engaging one embodiment of a retainer of the pump system.

FIGS. 19-23 illustrate other suitable embodiments of a pump system 310 (and, in the illustrated embodiment, a peristaltic pump system) and associated cassette 405. As seen in FIG. 19, the pump system 310 includes a platen 330 carrying a rotor 340 (broadly, a "bearing surface") and a retainer, indicated generally at 350. The illustrated rotor 340 has three peristalsis inducing rollers 345 (two being seen in FIG. 19). In this embodiment, a door 360 is hingely mounted to the platen 330 for movement between an opened position, which is illustrated in FIG. 19, and a closed position (not shown). The retainer 350 includes a sloped capture wall 355 (broadly, an "engagement member"). In one suitable embodiment, the capture wall 355 has a slope defined by angle α between about 10 degrees and about 80 degrees (FIG. 23). In other suitable embodiments, the slope of the capture wall 355 can be defined by an angle α between about 20 degrees and about 70 degrees, by an angle α between about 30 degrees and about 60 degrees, or by an angle α between about 40 and about 50 degrees. In the embodiment illustrated in FIG. 23, for example, the slope of the capture wall 355 is defined by an angle α of approximately 45 degrees.

The cassette 405, as seen in FIG. 22, includes a generally planar upper wall 475 and a sloped wall 408 (broadly, an "engagement member") extending downward from the upper wall. It is contemplated that the entire wall 408 may not be sloped, e.g., only a central portion thereof may be sloped and remain within the scope of this invention. A pair of barbs 337, 338 for receiving ends of the lumen (not shown) extends outward from the sloped wall 408. An inline valve, indicated generally at 435 is disposed on one of the barbs 337 and adapted to be received within the lumen. The inline valve 435 has a luminal plug 440, at least one valve port 445, and a sealing periphery 447.

Figure 4:
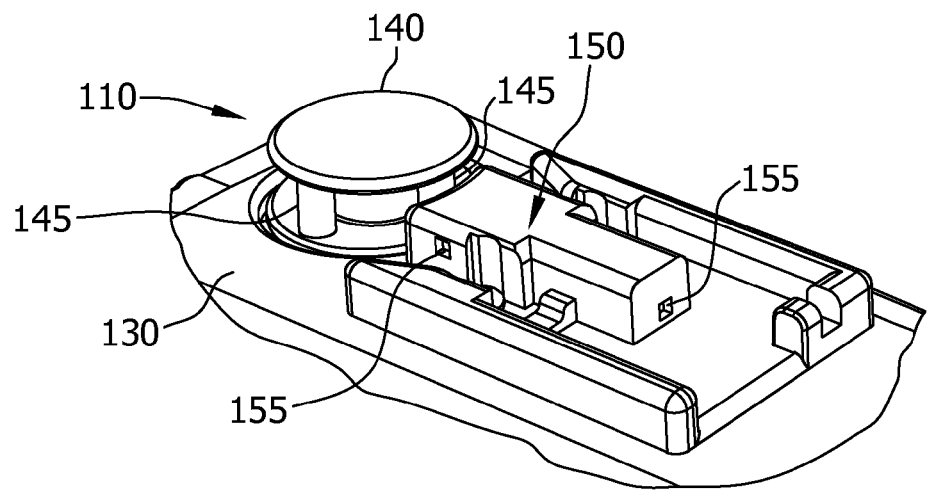
FIG. 4 is an enlarged fragmentary perspective illustrating the pump system of FIG. 2.

It is contemplated that the cassette 405 can include suitable latching clips (such as the latching clips 217 seen in FIG. 6) and the retainer 350 can include recesses (such as the recesses 155 seen in FIG. 4) adapted to receive the latching clips via a snap-fit connection.

Figure 20:
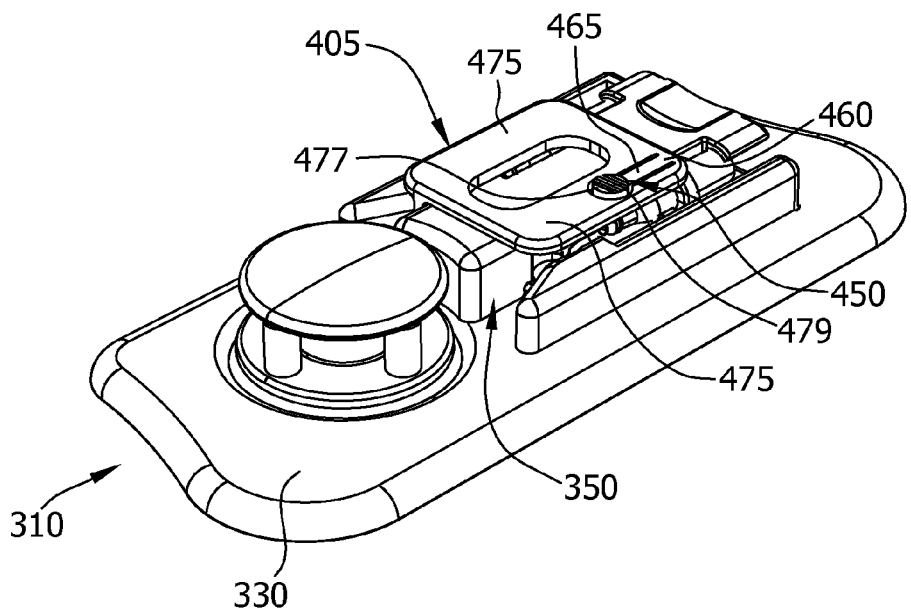
FIG. 20 is a rotated view of the pump system of FIG. 19 with a cassette of a feeding set engaged therewith.
Figure 21:
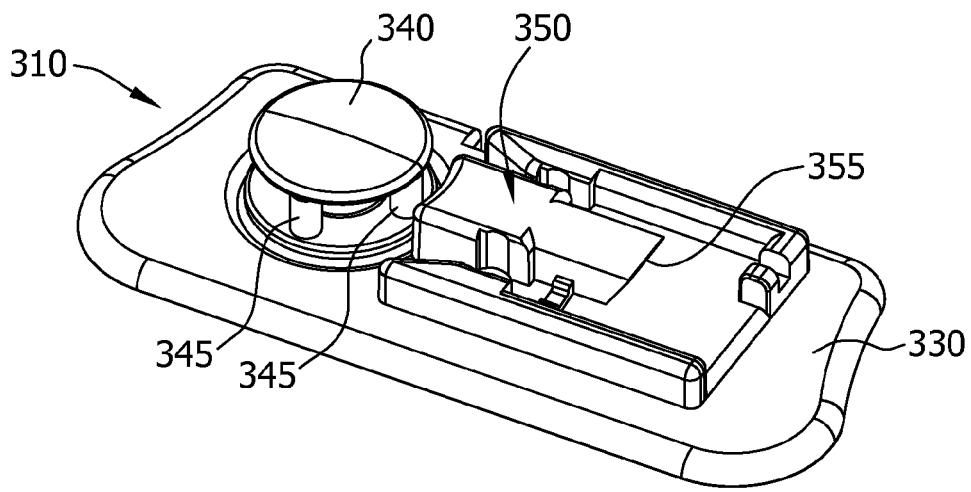
FIG. 21 is a rotated and tilted view of the pump system of FIG. 19.

As seen in FIG. 20, the cassette 405 also includes a deflectable lumen priming actuator, indicated generally at 450. The priming actuator 450 has a flex joint 460, a flexure arm 465 extending outward from the flex joint, and an actuation pad 425 formed on the flexure arm at a location spaced from the flex joint. The actuation pad 455 comprises an arcuate outer surface that is selected to be complementary to the shape of the lumen 210 (FIG. 22). With references still to FIG. 22, the flex joint 460 of this embodiment is covered by a reinforcement member 466 adapted to withstand and distribute dynamic stress and loading experienced during movement of the flexure arm 465 (i.e., actuation of the priming actuator 450). In the illustrated embodiment, the reinforcement member 466 has a suitable thickness, length, and width for extending across and thereby reinforcing the flex joint 260. It is contemplated, however, that the reinforcement member 466 can have other configurations (e.g., an elongate rib).

As illustrated in FIGS. 18 and 20, the priming actuator of this embodiment includes a thumb press 477 disposed on the flexure arm 465 opposite the actuation pad 425. The thumb press 477 has a concaved outer surface sized and shaped for receiving a digit (i.e., finger, thumb) of the user. In one suitable embodiment, for example, the concaved outer surface of the thumb press 477 has a radius of about 1.6 inches (about 40 mm). It is contemplated that the outer surface can have other suitable radii. The thumb press 477 also includes a tactile indicator in the form of a plurality of rounded nubs 479. The concaved outer surface and the nubs 479 cooperate to inhibit the user's digit from sliding off the thumb press 477 during use. In other words, the concaved outer surface and the nubs 479 cooperatively define an anti-slip feature. It is contemplated that tactile indicator can have other forms than the rounded nubs 479 illustrated herein.

In the illustrated embodiment, the lumen priming actuator 450 is formed integrally with the cassette 405. That is, the lumen priming actuator 450 and the cassette 405 are formed as a single-piece.

As illustrated in FIG. 23, the sloped wall 408 of the cassette 405 has a slope selected to be complementary to the sloped capture wall 455 of the retainer 450 such that when the cassette is mounted on the pump system 410, the sloped capture wall and the sloped wall are generally in face-to-face relationship. The lumen 210 biases (i.e., pulls) the cassette 405 toward the rotor 340 (FIG. 20). As a result, the lumen 210 biases (i.e., pulls) the sloped wall 408 of the cassette 405 against the capture wall 355 of the retainer 350. In one suitable embodiment, the lumen 210 holds the sloped wall 408 of the cassette 405 against the capture wall 355 of the retainer 350 with about 4 pounds of tensile force. It is contemplated, however, that the lumen 210 material and dimensions may be selected to provide more or less tensile force without departing from the scope of this invention.

Figure 24:
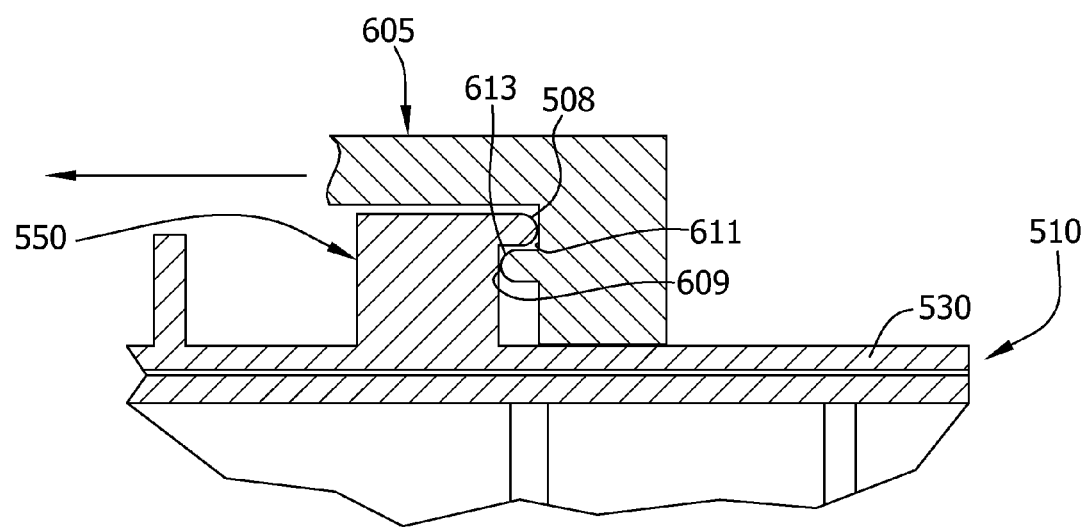
FIG. 24 is an enlarged fragmentary view similar to FIG. 23 but showing a cassette having a different embodiment engaging a different embodiment of a retainer of the pump system.

Referring now to FIG. 24, another suitable embodiment includes a retainer 550 mounted on a platen 530 of a pump system 510. The retainer 550 has an engagement member in the form of an overhang or upper retention member 508 formed thereon. A cassette 605 suitable for engaging the retainer 550 of this embodiment includes a corresponding engagement member in the form of an underfitment or projection, otherwise broadly referred to herein as a lower retention member 609 and a groove 611 formed on the cassette. The lower retention member 609 is sized to seat and extend beneath the upper retention member to inhibit upward movement of the cassette relative to the pump while the lumen is in tension. This inhibits inadvertent disconnection of the cassette from the pump. In the illustrated embodiment, the lower retention member 609 of the cassette in part defines a groove 611 for receiving the upper retention member 508 to provide more of a snap-fit connection of the cassette onto the pump. It is understood, however, that the groove 611 or other snap-fit arrangement may be omitted without departing from the scope of this invention.

To disengage the cassette 605 from the retainer 550, the cassette can be manually pulled upward so that the lower retention member 609 snaps past the upper retention member 508. This embodiment also provides tactile feedback in the form of both visual and audio cues to the user that the cassette 605 is properly engaged with the retainer 550. As illustrated in FIG. 24, at least a portion of a front surface 613 of the lower retention member 609 is sloped, or angled and more particularly slightly angled in the illustrated embodiment to facilitate movement of the lower retention member past the upper retention member 508.

In each of the embodiments described above, the feeding set may be removably and releasably engaged with and captured by the retainer for cooperative use and operation of the feeding set with the pump system. The various embodiments disclosed herein are suitable for use in many applications that involve manufacture, sale, and use of enteral feeding apparatus and the complementary enteral feeding sets for use in supplying liquid enteral products to patients in need of such supplemental feedings.

The configurations of the inventive enteral feeding apparatus may be modified to accommodate many types of enteral feeding sets that are suitable for use in healthcare facilities as well as in home care environments. Such enteral feeding sets may be adapted with various types of lumens to accommodate a variety of enterally deliverable, liquid nutritional products, which may have various viscosities and consistencies.

Such modifications and alternative arrangements may be further preferred and or optionally desired to establish compatibility with the wide variety of possible applications that are susceptible for use with the inventive and improved delivery sets and feeding sets for delivering the contemplated liquid nutritional products.

A method of connecting the feeding set 200 to the pump system 110 of the enteral feeding apparatus 100 is illustrated in FIG. 18. As seen therein, the peristalsis loop 220 of the lumen 210 of the feeding set 200 is looped around a portion of the rotor 140. The cassette 205 of the feeding set 200 and thereby the lumen 210 is then pulled in a direction away from the rotor 140 to apply a tension the lumen. In one suitable embodiment, the lumen 210 is placed under about 4 pounds of tensile force. It is understood, however, that the lumen 210 can be placed under different amounts of tensile force (i.e., more or less).

In the illustrated embodiment, the latching clips 217 of the cassette 205 are engaged via a snap-fit with the recesses 155 in the sidewall of the retainer 150. The projection 218 on the vertical wall 208 of the cassette 205 is received within the recess 155 in the back wall of the retainer 150 (FIG. 17). The lumen 210 biases (i.e., pulls) the cassette 205 toward the rotor 140. As a result, the lumen 210 biases (i.e., pulls) the vertical wall 208 of the cassette 205 against the back wall of the retainer 150 thereby holding the projection 218 within the recess 155. In other words, the tension in the lumen 210 urges the projection 218 of the cassette 205 in a direction of urging (illustrated by an arrow in FIGS. 23 and 24) and into engagement with the recess 155 of the retainer 150.

To feed a patient, the inlet tubing 225 is connected to a suitable enteral liquid source (i.e., a nutritional product) and the outlet tubing 230 is connected to a patient via a feeding tube (or other suitable feeding device). A user (e.g., a nurse, nurse's aid, nutritionists) then primes the feeding set 200 by depressing the priming actuator 250. Thereafter, the pump controller 170 is actuated to effect feeding of the enteral liquid to the patient.

After the feeding has been completed, the feeding set 200 can be disengaged from the pump system 110 and disposed of. That is, the feeding set 200 of the illustrated embodiment is disposed of after a single use.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A feeding set for a peristaltic pump system comprising:
a cassette configured for releasable connection to the pump system and having a deflectable lumen priming actuator formed integrally with the cassette for conjoint connection to and disconnection from the pump system with the cassette as a single unit, the priming actuator including an actuation pad and being moveable from a rest position to a deflected position;
a substantially flexible lumen coupled to the cassette, the lumen having an inlet, an outlet, and an extensible peristalsis loop;
an inline valve received within the lumen, the inline valve being arranged to obstruct fluid flow through the lumen;
wherein the actuation pad of the priming actuator is located proximate the inline valve in the rest position, the actuation pad being adapted to contact and apply a force to the lumen adjacent the inline valve when the priming actuator is moved to the deflected position, the force applied to the lumen being sufficient to establish at least one flow channel between the inline valve and the lumen.

2. The feeding set according to claim 1 wherein the actuation pad is disposed generally above the lumen and the inline valve in the rest position of the priming actuator.

3. The feeding set according to claim 1 wherein the inline valve is integral with the cassette.

4. The feeding set according to claim 3 wherein the cassette further comprises a pair of barbs for coupling the lumen to the cassette, the inline valve being integral with one of the barbs.

5. The feeding set according to claim 1 wherein the priming actuator comprises a flexure arm, the at least one actuation pad being disposed on the flexure arm.

6. The feeding set according to claim 1 wherein the actuation pad of the priming actuator has a concaved outer surface that is generally complementary to the shape of the lumen.

7. The feeding set according to claim 1 wherein the priming actuator comprises a thumb press with a tactile indicator in the form of a plurality of rounded nubs.

8. The feeding set according to claim 1 wherein the priming actuator and the cassette are a single-piece.

9. The feeding set according to claim 1 in combination with a pump system having a rotor wherein the extensible peristalsis loop is stretched about the rotor during use.

10. A feeding set for a peristaltic pump system comprising:
a cassette configured for releasable connection to the pump system and having a priming actuator formed integral with the cassette for conjoint connection to and disconnection from the pump system with the cassette as a single unit, the priming actuator being configured to be manually actuated from a rest position to a deflected position;
a lumen coupled to the cassette, the lumen having an inlet, an outlet, and an extensible peristalsis loop;
an inline valve received within and substantially obstructing fluid flow within the lumen;
wherein when the priming actuator is manually actuated to the deflected position the priming actuator acts on the lumen to thereby deform the lumen adjacent the inline valve to establish a fluid channel between the lumen and the inline valve.

11. The feeding set according to claim 10 wherein the priming actuator includes an actuation pad for acting on the lumen when the priming actuator is actuated to the deflected position.

12. The feeding set according to claim 11 wherein the priming actuator comprises a flexure arm, the actuation pad being disposed along a length of the flexure arm.

13. The feeding set according to claim 12 wherein the flexure arm includes a thumb press having a tactile indicator in the form of a plurality of rounded nubs.

14. The feeding set according to claim 10 wherein the priming actuator and the cassette are a single-piece.

15. The feeding set according to claim 10 wherein the priming actuator is disposed above the lumen and the inline valve when in the rest position.

16. The feeding set according to claim 10 in combination with a pump system having a rotor wherein the extensible peristalsis loop is stretched about the rotor during use.

17. A feeding set for a peristaltic pump system, the pump system having a rotor and a retainer, the feeding set comprising:
a cassette adapted for engagement with the retainer of the pump system, the cassette having a priming actuator formed integrally therewith, the priming actuator being moveable between a rest position and a deflected position, the priming actuator including a flexure arm and an actuation pad extending outward from the flexure arm;
a lumen coupled to the cassette, the lumen having an inlet, an outlet, and an extensible peristalsis loop, the peristalsis loop being confirmation for placement about the rotor;
an inline valve being received within the lumen and arranged to obstruct fluid flow within the lumen;
wherein the actuation pad of the priming actuator is disposed adjacent the inline valve in the rest position of the priming actuator, the actuation pad being moved into direction contact with the lumen adjacent the inline valve when the priming actuator is moved to the deflected position to establish at least one flow channel between the inline valve and the lumen.

18. The feeding set according to claim 17 wherein the cassette includes a generally vertical wall, the priming actuator extending generally perpendicular to the vertical wall.

19. The feeding set according to claim 18 wherein the cassette includes an upper wall extending outward and generally perpendicular to the vertical wall, the priming actuator being formed in the upper wall.

20. The feeding set according to claim 18 wherein the cassette includes a pair of barbs for coupling the lumen to the cassette, the barbs extending outward from the vertical wall.

21. The feeding set according to claim 20 wherein the inlet valve is integral with one of the barbs.

22. The feeding set according to claim 17 wherein the priming actuator comprises a thumb press with a tactile indicator.

23. The feeding set according to claim 17 wherein the priming actuator and the cassette are a single-piece.

24. The feeding set according to claim 17 wherein the priming actuator and the cassette are formed as separate pieces and permanently connected together.

25. The feeding set according to claim 17 wherein the priming actuator comprises a flex joint, a flexure arm extending outward from the flex joint, and a reinforcement member adapted to distribute dynamic stress and loading experienced during movement of the flexure arm about the flex joint.

* * * * *